US006231868B1

(12) United States Patent
Vakharia et al.

(10) Patent No.: US 6,231,868 B1
(45) Date of Patent: May 15, 2001

(54) METHOD FOR GENERATING NONPATHOGENIC INFECTIONS BIRNAVIRUS FROM SYNTHETIC RNA TRANSCRIPTS

(75) Inventors: Vikram N. Vakharia, Bowie; Kun Yao, College Park, both of MD (US)

(73) Assignee: University of Maryland-Biotechnology Institute, College Park, MD (US)

( * ) Notice: Subject to any disclaimer, the term of this patent is extended or adjusted under 35 U.S.C. 154(b) by 78 days.

(21) Appl. No.: 08/940,968

(22) Filed: Sep. 30, 1997

(51) Int. Cl.$^7$ .............................. A61K 39/12; C12N 7/01; C12N 7/04; C12N 15/40
(52) U.S. Cl. .................................. 424/204.1; 435/235.1; 435/236; 435/471; 435/320.1; 536/23.72; 424/816; 424/199.1
(58) Field of Search .................................. 435/236, 235.1, 435/472, 471, 320.1; 424/204.1, 199.1, 816; 536/23.72

(56) References Cited

U.S. PATENT DOCUMENTS

| | | |
|---|---|---|
| 4,530,831 | 7/1985 | Lütticken et al. . |
| 5,192,539 | 3/1993 | Van Der Marel et al. . |
| 5,310,678 | 5/1994 | Bingham et al. . |

FOREIGN PATENT DOCUMENTS

| | | |
|---|---|---|
| 0352835 A1 | 1/1990 | (EP) . |
| WO86/07060 | 12/1986 | (WO) . |
| WO91/05569 | 5/1991 | (WO) . |
| WO91/16925 | 11/1991 | (WO) . |
| WO93/03145 | 2/1993 | (WO) . |
| WO94/06904 | 3/1994 | (WO) . |
| WO95/26196 | 3/1995 | (WO) . |

OTHER PUBLICATIONS

Heppell et al, Journal of General Virology 76: 2091–2096, 1995.*
Mundt et al, Journal of Virology 71:5647–5651, 1997.*
Egbert Mundt & Hermann Müller, Virology, Complete Nucleotide Sequences of 5'–and 3'–Noncoding Regions of Both Genome Segments of Different Strains of Infectious Bursal Disease Virus, (1995), pp 10–18, vol. 209.
U. Spies & H. Müller, Journal of General Virology, Demonstration of enzyme activities required for cap structure formation in infectious bursal disease virus, a member of the birnavirus group, (1990), pp 977–981, vol. 71.
S. Zou & E.G. Brown, Virology, Identification of Sequence Elements Containing Signals for Replication and Encapsidation of the Reovirus M1 Genome Segment, (1992), pp 377–388, vol. 186.

(List continued on next page.)

*Primary Examiner*—Mary E. Mosher
(74) *Attorney, Agent, or Firm*—Arent Fox Kintner Plotkin & Kahn, PLLC

(57) ABSTRACT

A system for the generation of live, nonpathogenic Birnavirus such as infectious bursal disease virus (IBDV), a segmented double-stranded (ds)RNA virus of the Birnavirdae family, using synthetic transcripts derived from cloned DNA has been developed. Independent full-length cDNA clones were constructed which contained the coding and non-coding regions of RNA segments A and B of IBDV, respectively. Segment A was modified to prevent the expression of NS protein. Synthetic RNAs of both segments were produced by in vitro transcription of linearized plasmids with T7 RNA polymerase. Transfection of Vero cells with combined plus-sense transcripts of both segments generated infectious virus as early as 36 hours post-transfection. The development of a system for producing NS protein deficient IBDV will greatly facilitate studies of immunosuppression, and aid in the development of live attenuated vaccines for IBDV.

20 Claims, 14 Drawing Sheets

OTHER PUBLICATIONS

Mario I. Gorziglia & Peter L. Collins, Proc. Natl. Acad. Sci. USA, Intracellular amplification and expression of a synthetic analog of rotavirus genomic RNA bearing a foreign marker gene: Mapping cis–acting nucleotides in the 3'–noncoding region, Jul. 1992, pp 5784–5788, vol. 89.

Jean–Christophe Boyer & Anne–Lise Haenni, Virology, Infectious Transcripts and cDNA Clones of RNA Viruses, (1994), pp 415–426, vol. 198.

Sylvie Van Der Were, Jonathan Bradley, Eckard Wimmer, F. William Studier, & John J. Dunn, Proc. Natl, Acad. Sci. USA, Synthesis of infectious poliovirus RNA by purified T7 RNA polymerase, Apr. 1986, pp 2330–2334, vol. 83.

Wilem Luytjes, Mark Krystal, Masasyoshl Enami, Jeffrey D. Parvin, & Peter Palese, Cell, Amplification, Expression and Packing of a Foreign Gene : by Influenza Virus, Dec. 22, 1989, pp 1107–1113, vol. 59.

Matthias J. Schnell, Teshome Mebatsion & Karl–Klaus Conzelmann, The EMBO Journal, Infectious rabies viruses from cloned cDNA, (1994), pp 4195–4203. vol. 13.

Michael R. Roner, Lisa A. Sutphin, & Wolfgang K. Joklik, Virology, Reovirus RNA Is Infectious, (1990), pp 845–852, vol. 179.

Vikram N. Vakharia, Junkun He, Basheer Ahamed, David B. Snyder, Virus Research, Molecular basis of antigenic variation in infectious bursal disease virus, (1994), pp 265–273, vol. 31.

H. Müller, H. Lange & H. Becht, Virus Research, Formation, characterization and interfering capacity of a small plaque mutant and of incomplete virus particles of infectious bursal disease virus, (1986), pp 297–309, vol. 4.

Baoshan Chen, Gil H. Choi, & Donald L. Nuss, Science, Attenuation of Fungal Virulence by Synthetic Infectious Hypovirus Transcripts, Jun. 17, 1994, pp 1762–1764, vol. 264.

Peter Dobos, Virology, Protein–Primed RNA Synthesis In Vitro by the Virion–Associated RNA Polymerase Of Infectious Pancreatic Necrosis Virus, (1995), pp 19–25, vol. 208.

John T. Patton, Virus Research, Synthesis of Simian Rotavirus SA11 Double–Stranded RNA in A Cell–Free System, (1986/87), pp 217–233, vol. 6.

D.B. Snyder, V.N. Vakharia, S.A. Mengel–Whereat, G.H. Edwards, P.K. Savage, D. Lütticken, and M.A. Goodwin, Active Cross–Protection Induced by a Recombinant Baculovirus Expressing Chimeric Infectious Bursal Disease Virus Structural Proteins, Avian Diseases, (1994), vol. 38, No. 4 pp. 701–707.

V.N. Vakharia, Development of Recombinant Vaccines Against Infectious Bursal Disease, (1997), vol. 3. Biotechnology Annual Review, pp. 151–168.

E. Mundt and V.N. Vakharia, Synthetic Transcripts of Double–Stranded Birnavirus Genome are Infectious, Proc. Natl. Acad. Sci. USA (Oct., 1996), vol. 93 pp. 11131–11136.

Bayliss et al., A Comparison of the Sequences of Segment A of Four Infectious Bursal Disease Virus Strains and Identification of a Variable Region VP2. Journal of General Virology. vol. 71, pp. 1303–1312.

Mundt et al., Identification of a Novel Viral Protein in Infectious Bursal Disease Virus Infected Cells. Journal of General Virology. vol. 76, pp. 437–443.

Mundt et al., Complete Nucleotide Sequences of 5' and 3' Noncoding Regions of Both Genome Segments of Different Strains of Infectious Bursal Disease Virus. Virology vol. 209, pp. 10–18.

Spies et al. Nucleotide Sequence of Infectious Bursal Disease Virus Genome Segment A Delineates Two Major Open Reading Frame. Nucleic Acids Research vol. 17, No. 19, p. 7982.

Morgan et al., Sequence of the Small Double Stranded RNA Genomic Segment of Infectious Bursal Disease Virus and its Deduced 90kDa Product. Virology, vol. 163, pp. 240–242.

Michael Schonberg, Samuel C. Silverstein, Daniel H. Levin, & George Acs, Proc. Natl. Acad. Sci., Asynchronous Synthesis of the Complementary Strands of the Reovirus Genome, Feb. 1971, pp 505–508, vol. 68, No. 2.

Dayue Chen, Carl Q.–Y. Zeng, Melissa, J. Wentz, Mario Gorziglia, Mary K. Estes, & Robert F. Ramig., Journal of Virology, Template–Dependent, In Vitro Replication of Rotavirus RNA, (Nov. 1994, pp. 7030–7039, vol. 68, No. 11.

Jahrestagung Gesellschaft für Virologie 1997; Tagungsort: Universitat Hanburg 10.bis; Figs. 1–7; Mar. 13, 1997 (with English translation).

Bundesforschungsanstalt für Viruskrankheiten de Tiere; Jahresbericht 1996, p. 51, Published Apr. 16, 1997; (with English translation).

* cited by examiner

Fig. 2a  Fig. 2b  Fig. 2c
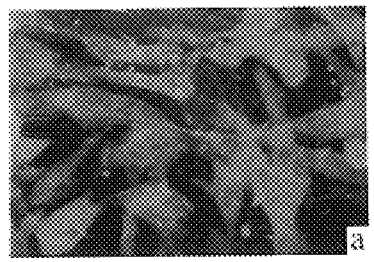 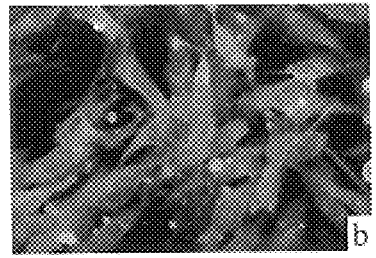 
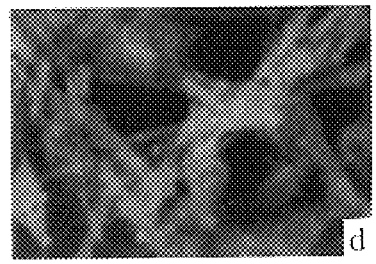 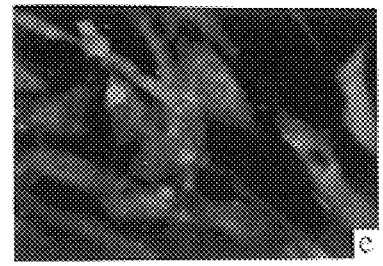 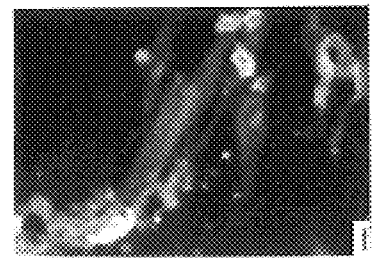
Fig. 2d  Fig. 2e  Fig. 2f

```
D78F              PRELIMINARY;    DNA;   3261 BP.
D78
NOTE: ORIGINAL SEQUENCE NAME WAS GLSDNA
SEQUENCE   3261 BP;    873 A;    909 C;    847 G;    632 T; 0 OTHER:
GGATACGATC GGTCTGACCC CGGGGGAGTC ACCCGGGGAC AGGCCGTCAA GGCCTTGTTC
CAGGATGGGA CTCCTCCTTC TACAACGCTA TCATTGATGG TTAGTAGAGA TCAGACAAAC
GATCGCAGCG ATGACAAACC TGCAAGATCA AACCCAACAG ATTGTTCCGT TCATACGGAG
CCTTCTGATG CCAACAACCG GACCGGCGTC CATTCCGGAC GACACCCTGG AGAAGCACAC
TCTCAGGTCA GAGACCTCGA CCTACAATTT GACTGTGGGG GACACAGGGT CAGGGCTAAT
TGTCTTTTTC CCTGGATTCC CTGGCTCAAT TGTGGGTGCT CACTACACAC TGCAGGGCAA
TGGGAACTAC AAGTTCGATC AGATGCTCCT GACTGCCCAG AACCTACCGG CCAGTTACAA
CTACTGCAGG CTAGTGAGTC GGAGTCTCAC AGTGAGGTCA AGCACACTTC CTGGTGGCGT
TTATGCACTA AACGGCACCA TAAACGCCGT GACCTTCCAA GGAAGCCTGA GTGAACTGAC
AGATGTTAGC TACAATGGGT TGATGTCTGC AACAGCCAAC ATCAACGACA AAATTGGGAA
CGTCCTAGTA GGGGAAGGGG TCACCGTCCT CAGCTTACCC ACATCATATG ATCTTGGGTA
TGTGAGGCTT GGTGACCCCA TTCCCGCAAT AGGGCTTGAC CCAAAAATGG TAGCCACATG
TGACAGCAGT GACAGGCCCA GAGTCTACAC CATAACTGCA GCCGATGATT ACCAATTCTC
ATCACAGTAC CAACCAGGTG GGGTAACAAT CACACTGTTC TCAGCCAACA TTGATGCCAT
CACAAGCCTC AGCGTTGGGG GAGAGCTCGT GTTTCAAACA AGCGTCCACG GCCTTGTACT
GGGCGCCACC ATCTACCTCA TAGGCTTTGA TGGGACAACG GTAATCACCA GGGCTGTGGC
CGCAAACAAT GGGCTGACGA CCGGCACCGA CAACCTTATG CCATTCAATC TTGTGATTCC
AACAAACGAG ATAACCCAGC CAATCACATC CATCAAACTG GAGATAGTGA CCTCCAAAAG
TGGTGGTCAG GCAGGGGATC AGATGTCATG GTCGGCAAGA GGGAGCCTAG CAGTGACGAT
CCATGGTGGC AACTATCCAG GGGCCCTCCG TCCCGTCACG CTAGTGGCCT ACGAAAGAGT
GGCAACAGGA TCCGTCGTTA CGGTCGCTGG GGTGAGCAAC TTCGAGCTGA TCCCAAATCC
TGAACTAGCA AAGAACCTGG TTACAGAATA CGGCCGATTT GACCCAGGAG CCATGAACTA
CACAAAATTG ATACTGAGTG AGAGGGACCG TCTTGGCATC AAGACCGTCT GGCCAACAAG
GGAGTACACT GACTTTCGTG AATACTTCAT GGAGGTGGCC GACCTCAACT CTCCCCTGAA
GATTGCAGGA GCATTCGGCT TCAAAGACAT AATCCGGGCC ATAAGGAGGA TAGCTGTGCC
GGTGGTCTCC ACATTGTTCC CACCTGCCGC TCCCCTAGCC CATGCAATTG GGGAAGGTGT
AGACTACCTG CTGGGCGATG AGGCACAGGC TGCTTCAGGA ACTGCTCGAG CCGCGTCAGG
AAAAGCAAGA GCTGCCTCAG GCCGCATAAG GCAGCTGACT CTCGCCGCCG ACAAGGGGTA
CGAGGTAGTC GCGAATCTAT TCCAGGTGCC CCAGAATCCC GTAGTCGACG GGATTCTTGC
TTCACCTGGG GTACTCCGCG GTGCACACAA CCTCGACTGC GTGTTAAGAG AGGGTGCCAC
GCTATTCCCT GTGGTTATTA CGACAGTGGA AGACGCCATG ACACCCAAAG CATTGAACAG
CAAAATGTTT GCTGTCATTG AAGGCGTGCG AGAAGACCTC CAACCTCCAT CTCAAAGAGG
ATCCTTCATA CGAACTCTCT CTGGACACAG AGTCTATGGA TATGCTCCAG ATGGGGTACT
TCCACTGGAG ACTGGGAGAG ACTACACCGT TGTCCCAATA GATGATGTCT GGGACGACAG
CATTATGCTG TCCAAAGATC CCATACCTCC TATTGTGGGA AACAGTGGAA ATCTAGCCAT
AGCTTACATG GATGTGTTTC GACCCAAAGT CCCAATCCAT GTGGCTATGA CGGGAGCCCT
CAATGCTTGT GGCGAGATTG AGAAAGTAAG CTTTAGAAGC ACCAAGCTCG CCACTGCACA
CCGACTTGGC CTTAGGTTGG CTGGTCCCGG AGCATTCGAT GTAAACACCG GGCCCAACTG
GGCAACGTTC ATCAAACGTT TCCCTCACAA TCCACGCGAC TGGGACAGGC TCCCCTACCT
CAACCTACCA TACCTTCCAC CCAATGCAGG ACGCCAGTAC CACCTTGCCA TGGCTGCATC
AGAGTTCAAA GAGACCCCCG AACTCGAGAG TGCCGTCAGA GCAATGGAAG CAGCAGCCAA
CGTGGACCCA CTATTCCAAT CTGCACTCAG TGTGTTCATG TGGCTGGAAG AGAATGGGAT
TGTGACTGAC ATGGCCAACT TCGCACTCAG CGACCCGAAC GCCCATCGGA TGCGAAATTT
TCTTGCAAAC GCACCACAAG CAGGCAGCAA GTCGCAAAGG GCCAAGTACG GGACAGCAGG
CTACGGAGTG GAGGCTCGGG GCCCCACACC AGAGGAAGCA CAGAGGGAAA AAGACACACG
GATCTCAAAG AAGATGGAGA CCATGGGCAT CTACTTTGCA ACACCAGAAT GGGTAGCACT
CAATGGGCAC CGAGGGCCAA GCCCCGGCCA GCTAAAGTAC TGGCAGAACA CACGAGAAAT
ACCGGACCCA AACGAGGACT ATCTAGACTA CGTGCATGCA GAGAAGAGCC GGTTGGCATC
AGAAGAACAA ATCCTAAGGG CAGCTACGTC GATCTACGGG GCTCCAGGAC AGGCAGAGCC
ACCCCAAGCT TTCATAGACG AAGTTGCCAA AGTCTATGAA ATCAACCATG GACGTGGCCC
AAACCAAGAA CAGATGAAAG ATCTGCTCTT GACTGCGATG GAGATGAAGC ATCGCAATCC
CAGGCGGGCT CTACCAAAGC CCAAGCCAAA ACCCAATGCT CCAACACAGA GACCCCCTGG
TCGGCTGGGC CGCTGGATCA GGACCGTCTC TGATGAGGAC CTTGAGTGAG GCTCCTGGGA
GTCTCCCGAC ACCACCCGCG CAGGTGTGGA CACCAATTCG GCCTTACAAC ATCCCAAATT
GGATCCGTTC GCGGGTCCCC T
```

Fig. 10

```
P2B              PRELIMINARY;   DNA;   2827 BP.
ORIGIN
SEQUENCE  2827 BP;    796 A;    770 C;    724 G;    537 T;   0 OTHER;
GGATACGATG  GGTCTGACCC  TCTGGGAGTC  ACGAATTAAC  GTGGCTACTA  GGGGCGATAC
CCGCCGCTGG  CCGCCACGTT  AGTGGCTCCT  CTTCTTGATG  ATTCTGCCAC  CATGAGTGAC
ATTTTCAACA  GTCCACAGGC  GCGAAGCACG  ATCTCAGCAG  CGTTCGGCAT  AAAGCCTACT
GCTGGACAAG  ACGTGGAAGA  ACTCTTGATC  CCTAAAGTTT  GGGTGCCACC  TGAGGATCCG
CTTGCCAGCC  CTAGTCGACT  GGCAAAGTTC  CTCAGAGAGA  ACGGCTACAA  AGTTTTGCAG
CCACGGTCTC  TGCCCGAGAA  TGAGGAGTAT  GAGACCGACC  AAATACTCCC  AGACTTAGCA
TGGATGCGAC  AGATAGAAGG  GGCTGTTTTA  AAACCCACTC  TATCTCTCCC  TATTGGAGAT
CAGGAGTACT  TCCCAAAGTA  CTACCCAACA  CATCGCCCTA  GCAAGGAGAA  GCCCAATGCG
TACCCGCCAG  ACATCGCACT  ACTCAAGCAG  ATGATTTACC  TGTTTCTCCA  GGTTCCAGAG
GCCAACGAGG  GCCTAAAGGA  TGAAGTAACC  CTCTTGACCC  AAAACATAAG  GGACAAGGCC
TATGGAAGTG  GGACCTACAT  GGGACAAGCA  AATCGACTTG  TGGCCATGAA  GGAGGTCGCC
ACTGGAAGAA  ACCCAAACAA  GGATCCTCTA  AAGCTTGGGT  ACACTTTTGA  GAGCATCGCG
CAGCTACTTG  ACATCACACT  ACCGGTAGGC  CCACCCGGTG  AGGATGACAA  GCCCTGGGTG
CCACTCACAA  GAGTGCCGTC  ACGGATGTTG  GTGCTGACGG  GAGACGTAGA  TGGCGACTTT
GAGGTTGAAG  ATTACCTTCC  CAAAATCAAC  CTCAAGTCAT  CAAGTGGACT  ACCATATGTA
GGTCGCACCA  AAGGAGAGAC  AATTGGCGAG  ATGATAGCTA  TCTCAAACCA  GTTTCTCAGA
GAGCTATCAA  CACTGTTGAA  GCAAGGTGCA  GGGACAAAGG  GGTCAAACAA  GAAGAAGCTA
CTCAGCATGT  TAAGTGACTA  TTGGTACTTA  TCATGCGGGC  TTTTGTTTCC  AAAGGCTGAA
AGGTACGACA  AAAGTACATG  GCTCACCAAG  ACCCGGAACA  TATGGTCAGC  TCCATCCCCA
ACACACCTCA  TGATCTCTAT  GATCACCTGG  CCCGTGATGT  CCAACAGCCC  AAATAACGTG
TTGAACATTG  AAGGGTGTCC  ATCACTCTAC  AAATTCAACC  CGTTCAGAGG  AGGGTTGAAC
AGGATCGTCG  AGTGGATATT  GGCCCCGGAA  GAACCCAAGG  CTCTTGTATA  TGCGGACAAC
ATATACATTG  TCCACTCAAA  CACGTGGTAC  TCAATTGACC  TAGAGAAGGG  TGAGGCAAAC
TGCACTCGCC  AACACATGCA  AGCCGCAATG  TACTACATAC  TCACCAGAGG  GTGGTCAGAC
AACGGCGACC  CAATGTTCAA  TCAAACATGG  GCCACCTTTG  CCATGAACAT  TGCCCCTGCT
CTAGTGGTGG  ACTCATCGTG  CCTGATAATG  AACCTGCAAA  TTAAGACCTA  TGGTCAAGGC
AGCGGGAATG  CAGCCACGTT  CATCAACAAC  CACCTCTTGA  GCACACTAGT  GCTTGACCAG
TGGAACCTGA  TGAGACAGCC  CAGACCAGAC  AGCGAGGAGT  TCAAATCAAT  TGAGGACAAG
CTAGGTATCA  ACTTTAAGAT  TGAGAGGTCC  ATTGATGATA  TCAGGGGCAA  GCTGAGACAG
CTTGTCCTCC  TTGCACAACC  AGGGTACCTG  AGTGGGGGGG  TTGAACCAGA  ACAATCCAGC
CCAACTGTTG  AGCTTGACCT  ACTAGGGTGG  TCAGCTACAT  ACAGCAAAGA  TCTCGGGATC
TATGTGCCGG  TGCTTGACAA  GGAACGCCTA  TTTTGTTCTG  CTGCGTATCC  CAAGGGAGTA
GAGAACAAGA  GTCTCAAGTC  CAAAGTCGGG  ATCGAGCAGG  CATACAAGGT  AGTCAGGTAT
GAGGCGTTGA  GGTTGGTAGG  TGGTTGGAAC  TACCCACTCC  TGAACAAAGC  CTGCAAGAAT
AACGCAGGCG  CCGCTCGGCG  GCATCTGGAG  GCCAAGGGGT  TCCCACTCGA  CGAGTTCCTA
GCCGAGTGGT  CTGAGCTGTC  AGAGTTCGGT  GAGGCCTTCG  AAGGCTTCAA  TATCAAGCTG
ACCGTAACAT  CTGAGAGCCT  AGCCGAACTG  AACAAGCCAG  TACCCCCCAA  GCCCCCAAAT
GTCAACAGAC  CAGTCAACAC  TGGGGGACTC  AAGGCAGTCA  GCAACGCCCT  CAAGACCGGT
CGGTACAGGA  ACGAAGCCGG  ACTGAGTGGT  CTCGTCCTTC  TAGCCACAGC  AAGAAGCCGT
CTGCAAGATG  CAGTTAAGGC  CAAGGCAGAA  GCCGAGAAAC  TCCACAAGTC  CAAGCCAGAC
GACCCCGATG  CAGACTGGTT  CGAAAGATCA  GAAACTCTGT  CAGACCTTCT  GGAGAAAGCC
GACATCGCCA  GCAAGGTCGC  CCACTCAGCA  CTCGTGGAAA  CAAGCGACGC  CCTTGAAGCA
GTTCAGTCGA  CTTCCGTGTA  CACCCCCAAG  TACCCAGAAG  TCAAGAACCC  ACAGACCGCC
TCCAACCCCG  TTGTTGGGCT  CCACCTGCCC  GCCAAGAGAG  CCACCGGTGT  CCAGGCCGCT
CTTCTCGGAG  CAGGAACGAG  CAGACCAATG  GGGATGGAGG  CCCCAACACG  GTCCAAGAAC
GCCGTGAAAA  TGGCCAAACG  GCGGCAACGC  CAAAAGGAGA  GCCGCTAACA  GCCATGATGG
GAACCACTCA  AGAAGAGGAC  ACTAATCCCA  GACCCCGTAT  CCCCGGCCTT  CGCCTGCGGG
GGCCCCC
```

Fig.11

```
D78B            PRELIMINARY;    DNA;    2827 BP.
ORIGIN
SEQUENCE   2827 BP;    795 A;     769 C;     725 G;     538 T;  0 OTHER;
GGATACGATG GGTCTGACCC TCTGGGAGTC ACGAATTAAC GTGGCTACTA GGGGCGATAC
CCGCCGCTGG CTGCCACGTT AGTGGCTCCT CTTCTTGATG ATTCTGCCAC CATGAGTGAC
ATTTTCAACA GTCCACAGGC GCGAAGCACG ATCTCAGCAG CGTTCGGCAT AAAGCCTACT
GCTGGACAAG ACGTGGAAGA ACTCTTGATC CCTAAAGTTT GGGTGCCACC TGAGGATCCG
CTTGCCAGCC CTAGTCGACT GGCAAAGTTC CTCAGAGAGA ACGGCTACAA AGTTTTGCAG
CCACGGTCTC TGCCCGAGAA TGAGGAGTAT GAGACCGACC AAATACTCCC AGACTTAGCA
TGGATGCGAC AGATAGAAGG GGCTGTTTTA AAACCCACTC TATCTCTCCC TATTGGAGAT
CAGGAGTACT TCCCAAAGTA CTACCCAACA CATCGCCCTA GCAAGGAGAA GCCCAATGCG
TACCCGCCAG ACATCGCACT ACTCAAGCAG ATGATTTACC TGTTTCTCCA GGTTCCAGAG
GCCAACGAGG GCCTAAAGGA TGAAGTAACC CTCTTGACCC AAAACATAAG GGACAAGGCC
TATGGAAGTG GGACCTACAT GGGACAAGCA ACTCGACTTG TGGCCATGAA GGAGGTCGCC
ACTGGAAGAA ACCCAAACAA GGATCCTCTA AAGCTTGGGT ACACTTTTGA GAGCATCGCG
CAGCTACTTG ACATCACACT ACCGGTAGGC CCACCCGGTG AGGATGACAA GCCCTGGGTG
CCACTCACAA GAGTGCCGTC ACGGATGTTG GTGCTGACGG GAGACGTAGA TGGCGACTTT
GAGGTTGAAG ATTACCTTCC CAAAATCAAC CTCAAGTCAT CAAGTGGACT ACCATATGTA
GGTCGCACCA AAGGAGAGAC AATTGGCGAG ATGATAGCTA TATCAAACCA GTTTCTCAGA
GAGCTATCAA CACTGTTGAA GCAAGGTGCA GGGACAAAGG GGTCAAACAA GAAGAAGCTA
CTCAGCATGT TAAGTGACTA TTGGTACTTA TCATGCGGGC TTTTGTTTCC AAAGGCTGAA
AGGTACGACA AAAGTACATG GCTCACCAAG ACCCGGAACA TATGGTCAGC TCCATCCCCA
ACACACCTCA TGATCTCCAT GATCACCTGG CCCGTGATGT CCAACAGCCC AAATAACGTG
TTGAACATTG AAGGGTGTCC ATCACTCTAC AAATTCAACC CGTTCAGAGG AGGGTTGAAC
AGGATCGTCG AGTGGATATT GGCCCCGGAA GAACCCAAGG CTCTTGTATA TGCGGACAAC
ATATACATTG TCCACTCAAA CACGTGGTAC TCAATTGACC TAGAGAAGGG TGAGGCAAAC
TGCACTCGCC AACACATGCA AGCCGCAATG TACTACATAC TCACCAGAGG GTGGTCAGAC
AACGGCGACC CAATGTTCAA TCAAACATGG GCCACCTTTG CCATGAACAT GCCCCTGCT
CTAGTGGTGG ACTCATCGTG CCTGATAATG AACCTGCAAA TTAAGACCTA TGGTCAAGGC
AGCGGGAATG CAGCCACGTT CATCAACAAC CACCTCTTGA GCACGCTAGT GCTTGACCAG
TGGAACTTGA TGAGACAGCC CAGACCAGAC AGCGAGGAGT TCAAATCAAT TGAGGACAAG
CTAGGTATCA ACTTTAAGAT TGAGAGGTCC ATTGATGATA TCAGGGGCAA GCTGAGACAG
CTTGTCCTCC TTGCACAACC AGGGTACCTG AGTGGGGGGG TTGAACCAGA ACAATCCAGC
CCAACTGTTG AGCTTGACCT ACTAGGGTGG TCAGCTACAT ACAGCAAAGA TCTCGGGATC
TATGTGCCGG TGCTTGACAA GGAACGCCTA TTTTGTTCTG CTGCGTATCC CAAGGGAGTA
GAGAACAAGA GTCTCAAGTC CAAAGTCGGG ATCGAGCAGG CATACAAGGT AGTCAGGTAT
GAGGCGTTGA GGTTGGTAGG TGGTTGGAAC TACCCACTCC TGAACAAAGC CTGCAAGAAT
AACGCAGGCG CCGCTCGGCG GCATCTGGAG GCCAAGGGGT TCCCACTCGA CGAGTTCCTA
GCCGAGTGGT CTGAGCTGTC AGAGTTCGGT GAGGCCTTCG AAGGCTTCAA TATCAAGCTG
ACCGTAACAT CTGAGAGCCT AGCCGAACTG AACAAGCCAG TACCCCCCAA GCCCCCAAAT
GTCAACAGAC CAGTCAACAC TGGGGGACTC AAGGCAGTCA GCAACGCCCT CAAGACCGGT
CGGTACAGGA ACGAAGCCGG ACTGAGTGGT CTCGTCCTTC TAGCCACAGC AAGAAGCCGT
CTGCAAGATG CAGTTAAGGC CAAGGCAGAA GCCGAGAAAC TCCACAAGTC CAAGCCAGAC
GACCCCGATG CAGACTGGTT CGAAAGATCA GAAACTCTGT CAGACCTTCT GGAGAAAGCC
GACATCGCCA GCAAGGTCGC CCACTCAGCA CTCGTGGAAA CAAGCGACGC CCTTGAAGCA
GTTCAGTCGA CTTCCGTGTA CACCCCCAAG TACCCAGAAG TCAAGAACCC ACAGACCGCC
TCCAACCCCG TTGTTGGGCT CCACCTGCCC GCCAAGAGAG CCACCGGTGT CCAGGCCGCT
CTTCTCGGAG CAGGAACGAG CAGACCAATG GGGATGGAGG CCCCAACACG GTCCAAGAAC
GCCGTGAAAA TGGCCAAACG GCGGCAACGC CAAAAGGAGA GCCGCTAACA GCCATGATGG
GAACCACTCA AGAAGAGGAC ACTAATCCCA GACCCCGTAT CCCCGGCCTT CGCCTGCGGG
GGCCCC
```

Fig. 12

METHOD FOR GENERATING NONPATHOGENIC INFECTIONS BIRNAVIRUS FROM SYNTHETIC RNA TRANSCRIPTS

BACKGROUND OF THE INVENTION

Infectious bursal disease virus (IBDV), a member of the Binaviridae family, is the causative agent of a highly immunosuppressive disease in young chickens (Kibenge, F. S. B., et al., *J. Gen. Virol.*, 69, 1757–1775 (1988)). Infectious bursal disease (IBD) or Gumboro disease is characterized by the destruction of lymphoid follicles in the bursa of Fabricius. In a fully susceptible chicken flock of 3–6 weeks of age the clinical disease causes severe immunosuppression, and is responsible for losses due to impaired growth, decreased feed efficiency, and death. Susceptible chickens less than 3 weeks old do not exhibit outward clinical signs of the disease but have a marked infection characterized by gross lesions of the bursa. Damage to the bursa ultimately causes immunodeficiency, which then leads to an increased susceptibility to other etiologic agents (Kibenge, F. S. B., et al., *J. Gen. Virol.*, 69, 1757–1775 (1988)) and interferes with effective vaccination against Newcastle disease, Marek's disease and infectious bronchitis disease viruses.

The virus associated with the symptoms of the disease is called infectious bursal disease virus (IBDV). IBDV is a pathogen of major economic importance to the nation and world's poultry industries. It causes severe immunodeficiency in young chickens by destruction of precursors of antibody-production B cells in the bursa of Fabricius. Immunosuppression causes increased susceptibility to other diseases.

There are two known serotypes of IBDV. Serotype I viruses are pathogenic to chickens whereas serotype 11 viruses infect chickens and turkeys but are nonpathgenic.

IBDV belongs to a group of viruses called Binaviridae which includes other bisegmented RNA viruses such as infectious pancreatic necrosis virus (fish), tellina virus and oyster virus (bivalve mollusks) and drosophila X virus (fruit fly). These viruses all contain high molecular weight (MW) double-stranded RNA genomes.

The capsid of the IBDV virion consists of several structural proteins. As many as nine structural proteins have been reported but there is evidence that some of these may have a precursor-product relationship (Kibenge, F. S. B., et al., *J. Gen. Virol.*, 69, 1757–1775 (1988)). The designation and molecular weights of the viral proteins (VP) are as shown below.

| Viral Protein | Molecular Weight |
| --- | --- |
| VP1 | 90 kDa |
| VP2 | 41 kDa |
| VP3 | 32 kDa |
| VP4 | 28 kDa |
| VP5 (NS) | 17 kDa |

The IBDV genome consists of two segments of double-stranded (ds)RNA that vary between 2827 (segment B) to 3261 (segment A) nucleotide base pairs (Mundt, E. et al., *Virology*, 209,10–18 (1995)). The larger segment A encodes a 110-kDa precursor protein in a single large open reading frame (polyprotein ORF) which is cleaved by autoproteolysis to form mature viral proteins VP2, VP3 and VP4 (Hudson, P. J. et al., *Nucleic Acids Res.*, 14, 5001–5012 (1986)). Segment A also encodes VP5, a 17-kDa nonstructural (NS) protein, from a small ORF partly preceding and overlapping the polyprotein ORF. However, this protein is not present in the virion and it is only detected in IBDV-infected cells (Mundt, e., et al., *J. Gen. Virol.*, 76, 437–443, 1995). Therefore, VP5 is designated as NS protein. The smaller segment B encodes VP1, a 97-kDa multifunctional protein with polymerase and capping enzyme activities (Spies, U., et al., *Virus Res.*, 8, 127–140 (1987); Spies, U., et al., *J. Gen. Virol.*, 71, 977–981 (1990)).

It has been demonstrated that the VP2 protein is the major host protective immunogen of IBDV, and that it contains the antigenic region responsible for the induction of neutralizing antibodies (Azad, et al., *Virology*, 161,145–152 (1987)). The region containing the neutralization site has been shown to be highly conformation-dependent. The VP3 protein has been considered to be a group-specific antigen because it is recognized by monoclonal antibodies directed against it from strains of both serotype I and 11 viruses. The VP4 protein appears to be a virus-coded protease that is involved in the processing of a precursor polyprotein of the VP2, VP3 and VP4 proteins (Jagadish, M. N., et al., *J. Virol.*,62, 1084–1087, 1988).

The nucleotide sequences for genome segments A and B of various IBDV strains have been published and the complete 5'- and 3'-noncoding sequences of both segments have been determined. The 5'-noncoding region of IBDV segments A and B contain a consensus sequence of 32 nucleotides, whereas the 3'-noncoding terminal sequences of both segments are unrelated, but conserved among IBDV strains of the same serotype (Mundt, E. et al., *Virology*, 209, 10–18 (1995)). These termini might contain sequences important in packaging and in the regulation of IBDV gene expression, as demonstrated for other dsRNA containing viruses such as mammalian and plant reoviruses, and rotaviruses (Anzola, et al., *Proc. Natl. Acad. Sci. USA*, 84, 8301–8305 (1987); Zou, S., et al., *Virology*, 186, 377–388 (1992); Gorziglia, M. I., et al., *Proc. Natl. Acad. Sci. USA*, 89, 5784–5788 (1992)).

In recent years, a number of infectious animal RNA viruses have been generated from cloned cDNA using transcripts produced by DNA-dependent RNA polymerase (Boyer, J. C., et al., *Virology*, 198, 415–426 (1994)). For example poliovirus, a plus-stranded RNA virus; influenza virus, a segmented negative-stranded RNA virus; rabies virus, a non-segmented negative-stranded RNA virus; all were recovered from cloned cDNAs of their respective genomes (van der Werf, S., et al., *Proc. Natl. Acad. Sci. USA*, 83, 2330–2334 (1986); Enami, M., et al., *Proc. Natl. Acad. Sci. USA*, 87, 3802–3805 (1990); Schnell, M. J., et al., *EMBO J.*, 13, 4195–4205 (1994)). For reovirus, it was shown that transfection of cells with a combination of ssRNA, dsRNA and in vitro translated reovirus products generated infectious reovirus when complemented with a helper virus from a different serotype (Roner, M. R., et al., *Virology*, 179, 845–852 (1990)).

Recently, one of the present inventors recovered a virus of segmented dsRNA genome from synthetic RNAs only. The reverse genetics system for bimavirus was developed by one of the present inventors who demonstrated that synthetic transcripts of infectious bursal disease virus (IBDV) genome are infectious (Proc. Natl. Acad. Sci. USA, 55:11131–11136, 1996). The present inventors have now determined that the 17 kDa nonstructural (NS)protein encoded by a minor open reading frame of segment A, is not required for viral replication in vitro or in vivo and plays an important role in viral pathogenesis.

Complete nucleotide sequences of the large segment A of various IBDV strains have been determined (Vakharia, V. N., et al., *Virus Res.,* 31, 265–273, 1994). In all cases, the small ORF is invariably present which codes for the 17-kDa NS protein. Recently, it was shown that NS protein is not required for viral replication in vitro (Mundt, E., et al., *J. Virol,* 71, 5647–5651). However, the function of this protein is still unknown. This protein is highly basic, cysteine-rich and conserved among all serotype I IBDV strains. In chicken anemia virus, another virus causing immunosuppression, an analogous basic, cysteine-rich 14-kDa protein was shown to cause apoptosis, and was implicated in pathogenesis (Noteborn, M. H. M., et al., *J. Virol.,* 68, 346–351, 1994). Since IBDV is also known to induce apoptosis in chicken blood lymphocytes (Vasconcelos, A. C., and Lam, K. M., *J. Gen. Virol.,* 75, 1803–1806,1994), the present inventors speculated that NS protein of IBDV may play a similar role in pathogenesis. Therefore, to study the function of NS protein in viral pathogenesis, the present inventors constructed a cDNA clone of IBDV segment A, in which the initiation codon of the NS gene was mutated to a stop codon. Using the reverse genetics system, a wild-type IBDV was generated, as well as a mutant IBDV that lacked the expression of the NS protein. The properties of the recovered wild-type IBDV and mutant IBDV in cell culture were compared and their pathological function in the natural host evaluated.

SUMMARY OF THE INVENTION

This invention relates to the infectious bursal disease virus (IBDV) that is associated with Gumboro disease of young chickens. More particularly, this invention relates to the generation of a NS protein deficient virus. The present invention will facilitate studies of immunosuppression and aid in the developement of live attenuated vaccines for IBDV.

As a first application of IBDV reverse genetics, and to study the function of NS protein in vivo, the present inventors generated an NS-protein deficient virus and demonstrated that the mutant virus can replicate in the bursa of inoculated chickens, but will not induce lesions. This implies that NS protein is directly involved in viral pathogenesis since the wild-type IBDV, expressing the NS protein, was able to elicit pathological response in the natural host. However, the mechanism by which the NS protein would exert its function remains to be seen.

The NS protein is highly conserved in all serotype I IBDV strains studied to date (greater than 95% identity). However, the NS protein of serotype 11 IBDV strains appears to be different, and shows 73% sequence identity. Since serotype If viruses are naturally avirulent and do not cause any pathological lesions in chicken (Ismail N. M., et al., 1988, Avian Dis. 32:757–759), it is conceivable that these residues may play a role in the pathogenicity of the virus.

The nonstructural proteins of animal viruses have been shown to play an important role in viral replication and pathogenesis. For example, in foot-and-mouth disease virus, a 16-kDa NS protein (leader protease) was shown to attenuate the virus in vitro and in vivo, but it was dispensable for viral replication (Brown, C. C., et al., 1996, J. Virol. 70:5638–5641; Piccone M. E., et al. 1995, J. Virol. 69:5376–5382). In chicken anemia virus (another immunosuppressive virus), a basic, cysteine and proline-rich, 14-kDa NS protein (VP3) was shown to cause apoptosis in lymphoblastoid T cells, and was implicated in pathogenesis (Noteborn, M. H. M., et al.,1994, A single chicken anemia virus protein induces apoptosis. J. Virol. 68, 346–351). However, this protein was found to be essential for viral replication. The present inventors have shown that NS protein of IBDV is not required for viral replication in vitro or in vivo. In addition, the results indicate that IBDV-induced cell death is significantly reduced due to the absence of NS protein expression.

In the absence of NS protein expression, the mutant virus seemed to be attenuated and had a titer that was one log lower than the wild-type virus. However, this did not affect the immune response to IBDV in the natural host. Using the present invention, it is possible to prepare novel, live-attenuated vaccines for IBDV, which are nonpathogenic to chickens.

DETAILED DESCRIPTION OF THE INVENTION

Synthetic transcripts derived from cloned DNA corresponding to the entire genome of a segmented dsRNA animal virus have been demonstrated to give rise to a replicating virus. The recovery of infectious virus after transfecting cells with synthetic plus-sense RNAs derived from cloned cDNA of a virus with a dsRNA genome (IBDV) completes the quest of generating reverse infectious systems for RNA viruses. A number of investigators have generated infectious animal RNA viruses from cloned cDNA (Boyer, J. C., et al., *Virology,* 198, 415–426 (1994)). Racaniello and Baltimore were first to rescue poliovirus, a plus-stranded RNA virus, using cloned cDNA (Racaniello, V. R. & Baltimore, D. (1981) *Science* 214, 916–919). Later, van der Werf et al. generated infectious poliovirus using synthetic RNA produced by T7 RNA polymerase on a cloned cDNA template ((van der Werf, S., et al., *Proc. Natl. Acad. Sci. USA,* 83, 2330–2334 (1986)). Enami et al. rescued influenza virus, a segmented negative-stranded RNA virus (Enami, M., et al., *Proc. Natl. Acad. Sci. USA,* 87, 3802–3805 (1990)); and Schnell et al. generated rabies virus, a nonsegmented negative-stranded RNA virus, from cloned cDNAs of their respective genomes (Schnell, M. J., et al., *EMBO J,* 13, 4195–4205 (1994)). Chen et al. demonstrated that the electroporation of fungal spheroplasts with synthetic plus-sense RNA transcripts, which correspond to the non-segmented dsRNA hypovirus, an uncapsidated fungal virus, yield mycelia that contain cytoplasmic-replicating dsRNA (Chen, B. Choi, G. H. & Nuss, D. L. (1994) *Science* 264, 1762–1764). Roner et a!. developed an infectious system for a segmented dsRNA reovirus by transfecting cells with a combination of ssRNA, dsRNA, in vitro translated reovirus products, and complemented with a helper virus of different serotype (Roner, M. R., Sutphin, L. A. & Joklik, W. K. (1990) *Virology* 179, 845–852). The resulting virus was discriminated from the helper virus by plaque assay. However, in this system the use of a helper virus was necessary. In contrast, the described reverse genetics system of IBDV does not require a helper virus or other viral proteins. Transfection of cells with plus-sense RNAs of both segments was sufficient to generate infectious virus (IBDV). In this regard, the system was comparable to other rescue systems of plus-stranded poliovirus and double-stranded hypovirus (van der Werf, S., et al.(1986) *Proc. Natl. Acad. Sci. USA* 83, 2330–2334; Chen, B., et al. (1994) *Science* 264, 1762–1764). The fate of the additional one and four nucleotides, respectively, transcribed at the 3'-end of segment A, was not determined. Obviously, this did not prevent the replication of the viral dsRNA. Similar effects have been observed in plus-stranded RNA viruses by different investigators (Boyer, J. C. et al.(1994) *Virology* 198, 415–426).

Transfection of plus-sense RNAs from both segments into the same cell was necessary for the successful recovery of IBDV. Transfected RNAs of both segments had to be translated by the cellular translation machinery. The polyprotein of segment A was presumably processed into VP2, VP3 and VP4 proteins, which form the viral capsid. The translated protein VP1 of segment B probably acted as a RNA-dependent RNA polymerase and transcribed minus-strands from synthetic plus-strands of both segments, and the reaction products formed dsRNA. Recently, Dobos reported that in vitro transcription by the virion RNA-dependent RNA polymerase of infectious pancreatic necrosis virus (IPNV), a prototype virus of the Binaviridae family, is primed by VP1 and then proceeds via an asymmetric, semiconservative, strand-displacement mechanism to synthesize only plus strands during replication of the viral genome (Dobos, P. (1995) Virology 208, 10–25). The present inventor's system showed that synthesis of minus strands must proceed on the plus strands. Whether the resulting transcribed minus-strand RNA serves as a template for the transcription of plus-strands or not remains the subject of further investigations.

To unequivocally prove that the infectious virus (IBDV) contained in supernatants of transfected cells was indeed derived from the synthetic transcripts, two recombinant viruses were generated containing the sequence tags in either segment A of strain D78 or segment B of strain P2. Restriction enzyme digests of the RT-PCR products and sequence analysis of the cloned DNA fragments verified the presence of these sequence tags in the genomic RNA segments.

The recovery of infectious virus (IBDV) demonstrated that only the plus-strand RNAs of both segments were sufficient to initiate replication of dsRNA. Thus, results are in agreement with the general features of reovirus and rotavirus replication, where the plus-strand RNAs serve as a template for the synthesis of progeny minus strands to yield dsRNA (Schonberg, M., et al. (1971) Proc. Natl. Acad. Sci. USA 68, 505–508; Patton, J. T. (1986) Virus Res. 6, 217–233; Chen, D., et al., (1994) J. Virol. 68, 7030–7039). However, the semiconservative strand displacement mechanisms proposed by Spies et al. and Dobos could not be excluded (Spies, U., et al. (1987) Virus Res. 8, 127–140; Dobos, P. (1995) Virology 208, 10–25). The development of a reverse genetics system for IBDV will greatly facilitate future studies of gene expression, pathogenesis, and help in the design of a new generation of live IBDV vaccines.

In order to study the function of the 17 kDa nonstructural (NS) protein in viral growth and pathogenesis, a cDNA clone of IBDV segment A was constructed, in which the first and only initiation codon (ATG) of NS protein A was mutated to a stop codon (TAG). Transfection of Vero cells with combined transcripts of either modified or unmodified segment A along with segment B gave rise to viable IBD viruses. When transfectant viruses were characterized by immunofluorescence assays using NS-specific antiserum, the mutant viorus did not yield a fluorescence signal, indicating a lack of NS protein expression. Further more, replication kinetics and cytotoxic effects of the mutant virus were compared with that of the wild type (WT) virus in vitro. The mutant virus grew to slightly lower titers than the wild-type (WT) virus and exhibited decreased cytotoxic and apoptosis effects in cell culture. To evaluate the characteristics of the recovered viruses in vivo, three-week-old chickens were inoculated with WT or mutant virus and their bursa analyzed for histopathological lesions. The WT virus caused microscopic lesions and atrophy of the bursa while the mutant virus failed to show any pathological lesions or clinical signs of disease. In both instances, the virus was recovered from the bursa and the presence or absence of mutation in the recovered viruses was confirmed by nucleotide sequence analysis of the NS gene. Although the mutant virus exhibited a delay in replication in vivo, it induced levels of IBDV neutralizing antibodies that were similar to those of the VT virus. In naddition, no reversion of mutation was detected in the mutant virus recovered from innoculated chickens. These results demonstrate that NS protein is dispensable for viral replication in vitro and in vivo and that it plays an important role in viral pathogenesis.

A mutant cDNA clone of segment A was constructed in which the first and only initiation codon of the NS gene was mutated to a stop codon (FIG. 1) to study the role of NS protein in IBDV. Thus, plasmid pUCD78NSΔ could encode only the precursor of the structural proteins (VP2, VP4, and VP 3). In addition, a full-length cDNA clone of segment B of the homologous IBDV strain D78 was constructed, which encoded VP1 protein (FIG. 1). Comparison of the deduced amino acid sequence of D78 segment B with P2 strain showed 99.97% amino acid identity, indicating that these two European strains are closely related. Coupled transcription and translation of the above plasmids in a rabbit reticulocyte system yielded protein products, which co-migrated with the marker IBDV proteins after fractionation on SDS-polyacrylamide gel and autoradiography.

Vero cells were transfected with combined transcripts of segments A and B to study the function of NS protein in viral replication. As expected, RNA transcripts of unmodified segments A and B from strain D78 generated recombinant D78 virus (rD78). When Vero cells were transfected with combined transcripts of modified segment A and B, it also generated a viable mutant virus (rD78NSΔ). To verify the mutation in rD78NSΔ virus, the genomic RNA was isolated and analyzed by reverse transcription polymerase chain reaction (RT-PCR) using a primer pair specific for segment A. Sequence analysis of the cloned PCR product confirmed the expected nucleotide mutations in the NS gene from the mutant virus.

Chicken embyo fibroblast (CEF) cells were infected with the recovered viruses and analyzed by immunofluorescence assay using NS-specific antiserum to detect the expression of NS protein. FIG. 2 shows the results of immunofluorescence staining of IBDV-infected cells. Cells infected with rD78 virus expressed NS protein and gave a positive immunofluorescence signal (FIG. 2c, f). However, cells infected with mutant rD78NSΔ virus failed to give any fluorescence signal, indicating the absence of NS protein expression, even after the tenth passage (FIG. 2b, e). No fluorescence was detected in the mock-infected cells (FIG. 2a, d). These results indicate that NS protein is not required for replication in cell culture, which is in agreement with the recent report of Mundt et al. (Mundt, E., et al., J.Virol., 71: 5647–5651, 1997).

In order to determine the replication kinetics of D78, rD78, and rD78NSΔ, chicken embryo fibroblast (CEF) cells were infected with each virus and their titers were determined by plaque assay. FIG. 3A depicts the growth curve of each virus (expressed as log PFU/ml) at different days post-infection. The results indicate that the mutant virus (lacking the expression of NS protein) replicated somewhat slower and had a titer that was one log lower than the wild-type (D78) or recovered (rD78) virus at six days post-infection. However, the plaques produced by the mutant virus were similar in size to those produced by the parental virus. Furthermore, the transfectant viruses were purified by CsCl gradient, and their proteins were analyzed by Western blot analysis using IBDV antiserum. Qualitatively, viral structural proteins (VP2, VP4 and VP3) produced by the mutant virus were identical to the proteins synthesized by the recovered virus (rD78) or the wild-type D78 virus.

The cytopathogenicity of rD78NSΔ IBDV was compared with that of rD78 or D78 IBDV in chicken embryo fibroblast (CEF) cells. FIG. 3B depicts the cytotoxic effect of these viruses at different days post-infection. Chicken embryo fibroblast (CEF) cells infected with parental D78 or rD78 IBDV showed a decrease in cell viability (22 to 40%) when compared to the cells infected with rD78NSΔ IBDV (50 to 65%). At 3 days post-infection, chicken embryo fibroblast (CEF) cells exhibited considerable cell death due to IBDV replication, which coincided with the virus titer (FIG. 3A). The viability of chicken embryo fibroblast (CEF) cells infected with the mutant virus (rD78NSΔ) was almost two-fold greater than that of cells infected with the wild-type (D78) or recovered(rD78) virus at 6 days post-infection. No significant cytotoxic effect was detected in the mock-infected cells.

IBDV is known to induce apoptosis in chicken blood lymphocytes. In order to determine the apoptotic effects of rD78 and rD78NSΔ IBDV in chicken embryo fibroblast (CEF) cells, the cells were infected with each virus at an Multiplicity of infection (MOI) of 1, harvested at different time points, and analyzed by Terminal deoxynucleotide transferase-dUTP Nick-End-Labeling (TUNEL) assay (FIG. 4). The results indicate that the cells infected with rD78 induced a significant amount of apoptosis, as evidenced by green fluorescence signal (FIG. 4c, f, and i). In contrast, apoptosis induced by the mutant rD78NSΔ virus was significantly lower than that produced by rD78 (FIG. 4b, e, and h). No appreciable level of apoptosis was detected in the mock-infected cells (FIG. 4a, d, and g). These results indicate that IBDV-induced cell death is apparently reduced due to the absence of NS protein expression.

In order to study the role of NS protein in viral pathogenesis, groups of 3-week-old chickens were mock inoculated or inoculated with either rD78 or rD78NSΔ virus, and their bursa analyzed for pathological lesions. Table 1 summarizes the results of histopathological examination of bursa obtained from different groups of chickens at selected days post-infection. Chickens inoculated with rD78 virus showed gross bursal lesions (bursal atrophy) at 6 and 9 days post inoculation. In addition, this virus produced microscopic lesions in the bursa at 2, 4, 6 and 9 days post inoculation, as indicated in Table 1. No gross or microscopic lesions were observed in chickens that were inoculated with the control medium or rD78NSΔ virus. Moreover, histopathologic sections of bursa derived from the control or rD78NSΔ groups were similar and had normal follicles and follicular connective tissues as shown in FIG. 5a and b. However, the sections derived from rD78 group showed lymphocytic necrosis and follicular (B-lymphocytes) depletion at 2, 4, 6 and 9 days post-inoculation. Subsequently, extensive accumulation of mononuclear cells resulted in the loss of distinction between cortex and medulla of infected bursal section, as shown in FIG. 5c. These results clearly indicate that the mutant virus does not cause bursal lesions.

Bursa from each group were pooled, homogenized in M199 medium, and the filtered homogenate analyzed for infectivity in chicken embryo fibroblast (CEF) cells in order to detect the presence of virus in the bursa of infected chickens. After 2–3 days post-infection, the virus was detected (as evidenced by cytopathic effect) in cells infected with the homogenates of rD78 or rD78NSΔ groups at 2, 4, 6, and/or 9 days post-inoculation (Table 2). No virus was detected in the 21-day bursal homogenate, indicating that the virus was cleared from the bursa. As expected, no virus was detected in the control group. To verify the presence or absence of mutation in the recovered viruses, whole cell nucleic acid was isolated from each bursal homogenate and analyzed by RT-PCR as described earlier. As expected, a 555-bp fragment was amplified from the homogenates of rD78 and rD78NSΔ groups at 2, 4, 6, and/or 9 days post-inoculation, but not from the control group or from the 21-day bursal homogenates (Table 2). In addition, the presence of viral antigen in the bursal sections of different groups was also confirmed by immunofluorescence assay using IBDV antiserum.

The present inventors propagated the viruses in chicken embryo fibroblast (CEF) cells (up to ten passages), isolated whole cell nucleic acids, and amplified the NS gene by RT-PCR to determine the genetic stability of the transfectant viruses in vitro. Sequence analysis of the cloned PCR product confirmed the expected nucleotide mutations in the NS gene of the mutant virus, whereas no mutation was detected in the PCR product of rD78 virus. Similarly, to determine the genetic stability of these viruses in vivo, chickens were inoculated with transfectant viruses, and their bursa collected at various days post-infection. Total nucleic acid was extracted from bursal tissue, and the NS gene amplified by RT-PCR using a primer pair specific for segment A. Sequence analysis of the NS gene from the mutant virus revealed the presence of two mutations (97 A→T, 98 T→A) in bursal samples collected at 2, 4, 6, and 9 days post-infection. As expected, not a single nucleotide mutation as detected in the NS gene of the bursal materials infected with rD78 virus. These results clearly demonstrate that the mutant virus replicated in the bursa f chickens but did not revert to the wild-type IBDV.

Chickens were inoculated with equal amounts ($5 \times 10^3$ PFU) of rD78 nd rD78NSΔ IBDV to compare the replication behavior of recovered viruses in vivo. Virus titers in the bursa from each group at different time points were determined by plaque assay on chicken embryo fibroblast (CEF) cells (Table 3). The results indicate that rD78NSΔ virus replicated at a lower rate than rD78 virus and its virus titer reached a peak at day 6 (versus day 2 for rD78 virus), suggesting a possible role of NS protein during in vivo replication. Indirect IFA was performed on bursal sections of chickens infected with rD78 and rD78NSΔ IBDV, using NS-specific antiserum. Bursal sections from chickens infected with the mutant virus at 2 and 4 days post-infection did not give a fluorescence signal, confirming the lack of NS protein expression. These results clearly show that the mutant virus, lacking the expression of NS protein, efficiently replicated in the bursa of chickens.

To compare the immune response induced by the recovered rD78 and rD78NSΔ IBDV, chickens were inoculated with the recovered viruses, bled at 14 and 21 days post-inoculation, and their sera analyzed by virus neutralization (ON) test. VN antibody titers of the sera are shown in Table 3. Although rD78NSΔ virus replicated at a lower rate than rD78 virus and its titer peaked at day 6, it induced VN titers that were comparable to the recovered D78 virus at 14 and 21 days post-inoculation. These results indicate that the mutant virus, which is deficient in producing NS protein, does not affect the immune response to IBDV in the natural host.

As used in the present application, the term "synthetic" as applied to nucleic acids indicates that it is a man made nucleic acid in contrast to a naturally occurring nucleic acid. The term implies no limitation as to the method of manufacture, which can be chemical or biological as long as the method of manufacture involves the intervention of man.

The term "cDNA" is intended to encompass any cDNA containing segments A and B and the 5' and 3' noncoding regions of segments A and B.

The term "infectious" as applied to viruses indicates that the virus has the ability to reproduce. The virus can be pathogenic or nonpathogentic and still be infectious.

The present invention provides a system for the generation of NS protein defficient infectious bursal disease virus using synthetic RNA transcripts. This system can be used to study immunosuppression and for the design of a new generation of live and inactivated IBDV vaccines.

The present invention provides a recombinant vector containing at least one copy of the cDNA according to the present invention. The recombinant vector may also comprise other necessary sequences such as expression control sequences, markers, amplifying genes, signal sequences, promoters, and the like, as is known in the art. Useful vectors for this purpose are plasmids, and viruses such as baculoviruses, herpes virus (HVT) and pox viruses, e.g., fowl pox virus, and the like.

Also provided herein is a host cell transformed with the recombinant vector of the present invention or a host cell transfected with the synthetic RNA of the present invention. The host cell may be a eukaryotic or a prokaryotic host cell. Suitable examples are E. col, insect cell lines such as Sf-9, chicken embryo fibroblast (CEF) cells, chicken embryo kidney (CEK) cells, African green monkey Vero cells and the like.

Also part of this invention is an NS protein defficient IBDV poultry vaccine comprising a poultry protecting amount of a recombinantly produced virus or portion of a virus, wherein the virus does not induce pathological lesions.

The virus can be further modified or inactivated by chemical or physical means. Chemical inactivation can be achieved by treating the virus with, for example, enzymes, formaldehyde, β-propiolactone, ethylene-imine or a derivative thereof, an organic solvent (e.g. halogenated hydrocarbon) and or a detergent. If necessary, the inactivating substance can be neutralized after the virus has been inactivated. Physical inactivation can be carried out by subjecting the viruses to radiation such as UV light, X-radiation, or y-radiation.

The virus can also be modified by known methods including serial passage, deleting further sequences of nucleic acids and site directed mutagenesis either before or after production of the infectious virus.

The virus can be a chimeric recombinant virus which contains epitopic determinants for more than one strain of IBDV. Epitopic determinants as discussed in the present document are amino acids or amino acid sequences which correspond to epitopes recognized by one or more monoclonal antibodies. Since VP2 protein is the major host protective immunogen of IBDV, the chimeric virus would include VP2 immunogens from at least two different IBDV strains in addition to the modified NS gene according to the present invention. Methods for producing a chimeric virus are disclosed in Vakharia, *Biotechnology Annual Review Volume* 3,151–168, 1997; Snyder et al., *Avian Diseases,* 38:701–707,1994; and WO 95/26196. Strains suitable for use in producing a chimeric IBD virus include but are not limited to IM+, IM, STC, 2512 (Winterfield), Edgar, Md., BVM, 1048-E, D78, 8903, E/Del, A/Del, D/Del, GLS, DS326, S977, and RS593.

Physiologically acceptable carriers for vaccination of poultry are known in the art and need not be further described herein. In addition to being physiologically acceptable to the poultry the carrier must not interfere with the immunological response elicited by the vaccine and/or with the expression of its polypeptide product.

Other additives, such as adjuvants and stabilizers, among others, may also be contained in the vaccine in amounts known in the art. Preferably, adjuvants such as aluminum hydroxide, aluminum phosphate, plant and animal oils, and the like, are administered with the vaccine in amounts sufficient to enhance the immune response to the IBDV. The amount of adjuvant added to the vaccine will vary depending on the nature of the adjuvant, generally ranging from about 0.1 to about 100 times the weight of the IBDV, preferably from about 1 to about 10 times the weight of the IBDV.

The vaccine of the present invention may also contain various stabilizers. Any suitable stabilizer can be used including carbohydrates such as sorbitol, mannitol, starch, sucrose, dextrin, or glucose; proteins such as albumin or casein; and buffers such as alkaline metal phosphate and the like. A stabilizer is particularly advantageous when a dry vaccine preparation is prepared by lyophilization.

The vaccine can be administered by any suitable known method of inoculating poultry including nasally, ophthalmically, by injection, in drinking water, in the feed, by exposure, and the like. Preferably, the vaccine is administered by mass administration techniques such as by placing the vaccine in drinking water or by spraying the animals' environment. When administered by injection, the vaccines are preferably administered parenterally. Parenteral administration as used herein means administration by intravenous, subcutaneous, intramuscular, or intraperitoneal injection.

The vaccine of the present invention is administered to poultry to prevent IBD anytime before or after hatching. Preferably, the vaccine is administered prior to the time of birth and after the animal is about 34 weeks of age. Poultry is defined to include but not be limited to chickens, roosters, hens, broilers, roasters, breeders, layers, turkeys and ducks.

The vaccine may be provided in a sterile container in unit form or in other amounts. It is preferably stored frozen, below −20° C., and more preferably below −70° C. It is thawed prior to use, and may be refrozen immediately thereafter. For administration to poultry, the recombinantly produced virus may be suspended in a carrier in an amount of about $10^4$ to $10^7$ pfu/ml, and more preferably about $10^5$ to $10^8$ pfu/ml in a carrier such as a saline solution. The inactivated vaccine may contain the antigenic equivalent of $10^4$ to $10^7$ pfu/ml suspended in a carrier. Other carriers may also be utilized as is known in the art. Examples of pharmaceutically acceptable carriers are diluents and inert pharmaceutical carriers known in the art. Preferably, the carrier or diluent is one compatible with the administration of the vaccine by mass administration techniques. However, the carrier or diluent may also be compatible with other administration methods such as injection, eye drops, nose drops, and the like.

The invention also can be used to produce combination vaccines with the IBDV material. The IBDV material can be combined with antigen material of Newcastle Disease Virus Infectious Bronchitis virus, Reo virus, Adeno virus and/or the Marek virus.

The foregoing embodiments of the present invention are further described in the following Examples. However, the present invention is not limited by the Examples, and variations will be apparent to those skilled in the art without departing from the scope of the present invention.

BRIEF DESCRIPTION OF THE DRAWINGS

FIG. 2 shows immunofluorescence staining of IBDV-infected cells used to detect NS protein expression. Chicken embryo fibroblast (CEF) cells were infected with either rD78NSΔ mutant virus stock of the first passage (b) and the tenth passage (e) or rD78 virus stock of the first passage (c) and the tenth passage (f) at an multiplicity of infection (MOI) of 1. Uninfected chicken embryo fibroblast (CEF) were used as negative controls (a, d). After 24 h post-infection, the cells were fixed, and analyzed by immunofluorescence staining with rabbit anti-NS protein serum. (Magnifications are X400)

FIG. 10 shows the DNA sequence of pUC19FLAD78 [SEQ ID NO: 23].

FIG. 11 shows the DNA sequence of pUC18FLBP2 [SEQ ID NO: 24].

FIG. 12 shows the DNA sequence of pUCD78B [SEQ ID NO: 25].

EXAMPLES

Example 1
Generation of Infectious Virus from Synthetic RNAs

Viruses and Cells.

Two serotype I strains of IBDV, the attenuated P2 strain from Germany and the vaccine strain D78 (Intervet International), were propagated in chicken embryo fibroblast (CEF) cells and purified as described (Mundt, E. & Müller, H. (1995) Virology 209, 10–18, Vakharia, V. N., He, J., Ahamed, B. & Snyder, D. B. (1994) Virus Res. 31, 265–273). Vero cells were grown in M199 medium supplemented with 5% fetal calf serum (FCS) and used for transfection experiments. Further propagation of the recovered virus and immunofluorescence studies were carried out in Vero cells as described (Mundt, E., Beyer, J. & Müller, H. (1995) J. Gen. Virol. 76, 437–443). For plaque assay, monolayers of secondary CEC were prepared and used as described previously (Müller, H., Lange, H. & Becht, H. (1986) Virus Res. 4, 297–309).

Figure 6A:
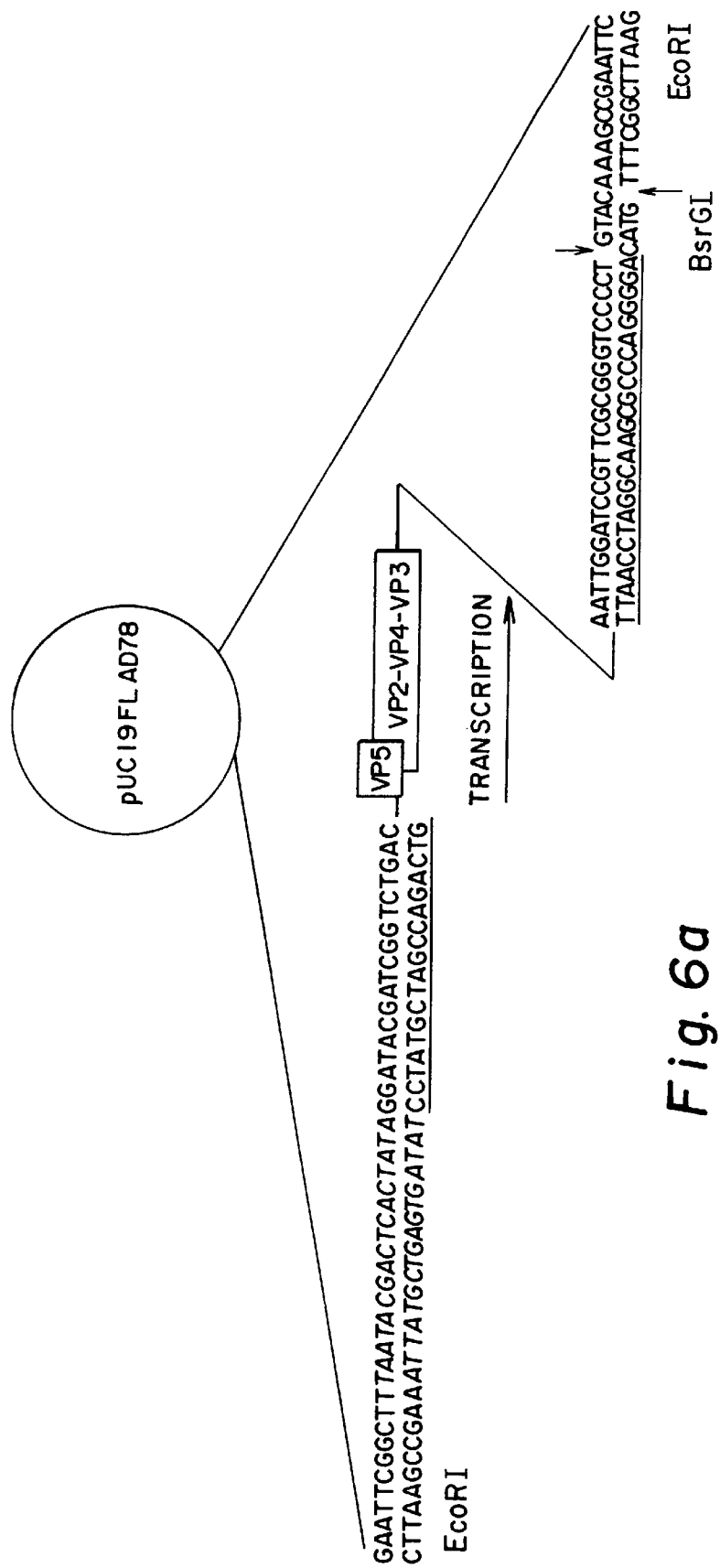
FIG. 6 shows a schematic diagram of cDNA constructs used for synthesis of plus-sense ssRNAs of IBDV with T7 RNA polymerase. Construct pUC19FLAD78 [SEQ ID NO: 21] contains the full-length cDNA of segment A of IBDV strain D78. Segment A of IBDV encodes the polyprotein (VP2-VP4-VP3), and VP5 protein (NS). Plasmid pUC18FLBP2 [SEQ ID NO: 22] contains the cDNA of segment B of strain P2 which encodes the RNA-dependent RNA polymerase (VP1). Virus specific sequences are underlined and the T7 promoter sequences are italicized. Restriction sites are shown in boldface and identified. The cleavage sites of the linearized plasmids are shown by vertical arrows and the transcription directions are marked by horizontal arrows.
Figure 6B:
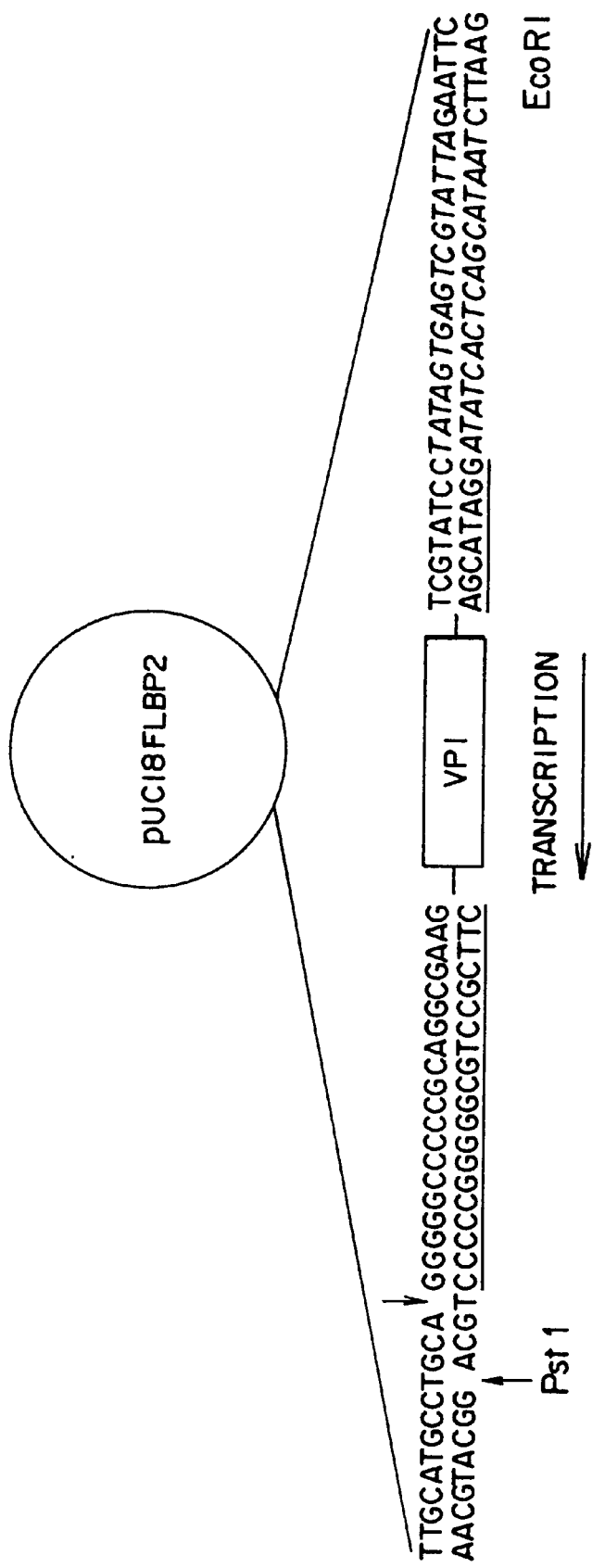
Figure 7:
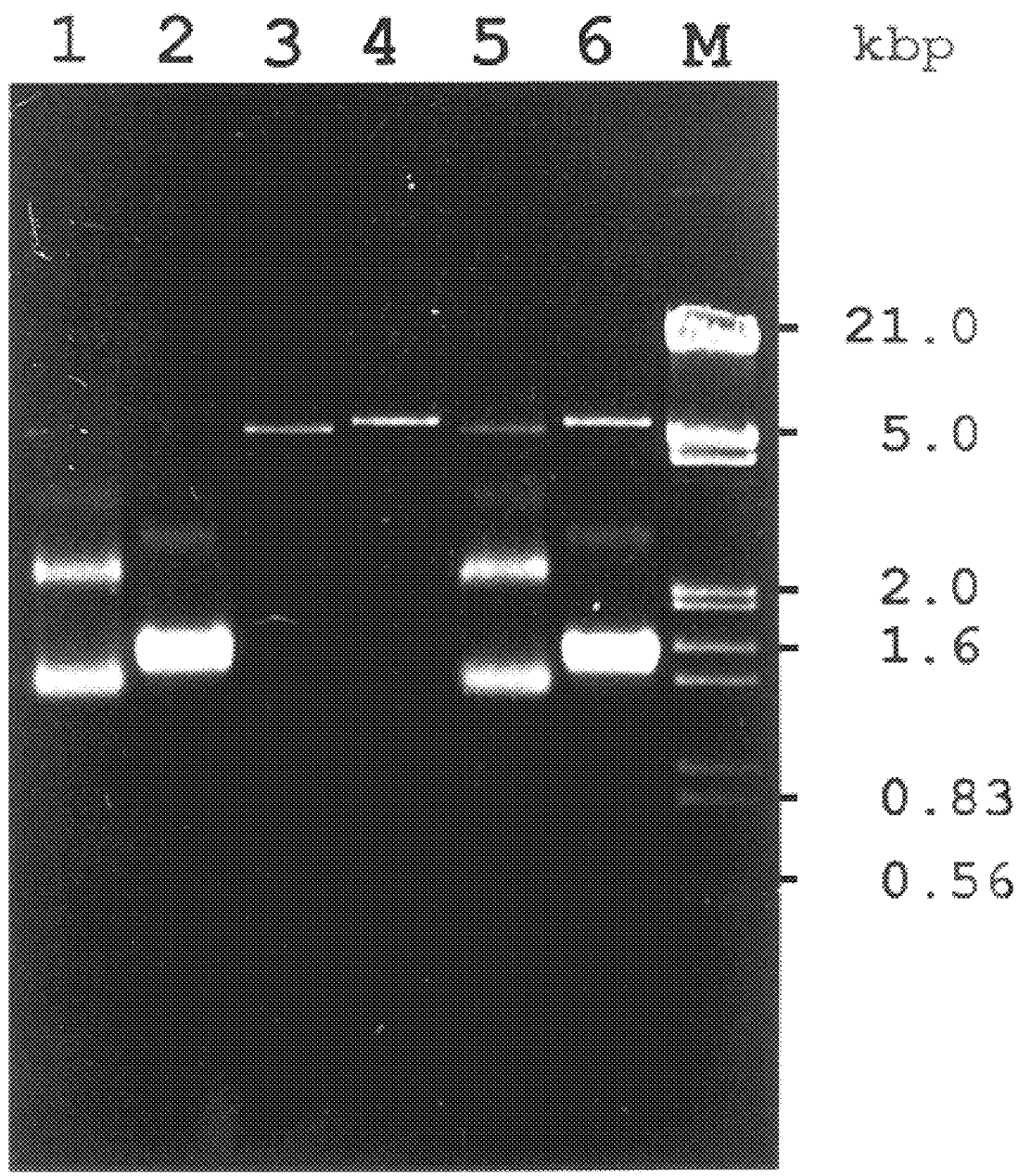
FIG. 7 shows an analysis of the transcription reaction products that were used for transfection of Vero cells. Synthetic RNAs transcribed in vitro using T7 RNA polymerase and linearized plasmids pUC19FLAD78 containing the cDNA of segment A of IBDV strain D78 (lanes 2, 4 and 6) and pUC18FLBP2 containing the cDNA of segment B of strain P2 (lanes 1, 3 and 5), respectively. After transcription, the reaction mixtures were either treated with DNase (lanes 1 and 2), RNase (lanes 3 and 4) or left untreated (lanes 5 and 6). The reaction products (2 pi) were analyzed on 1% agarose gel. Lambda DNA, digested with Hind III/EcoR I, was used as a marker (lane M).
Figure 8:
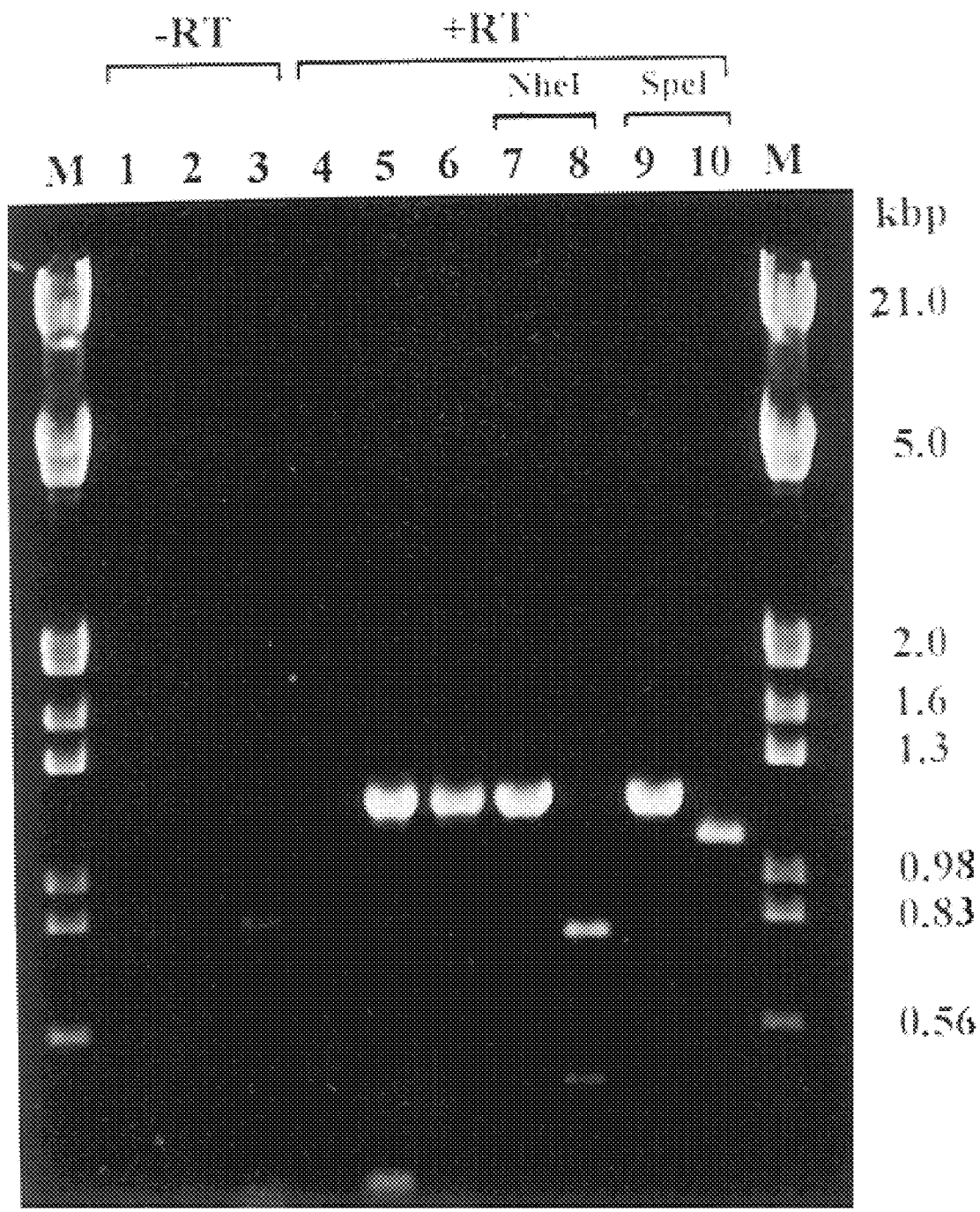
FIG. 8 is an analysis of the RT-PCR products for identification of the sequence tags in segment A of the transfectant viruses. Genomic RNA isolated from transfectant viruses was amplified by RT-PCR using segment A specific primers 5-'ATGACAAACCTGCAAGAT-3' [SEQ ID NO: 1] (nucleotide positions 131–148) and 5'-CATGGCTCCTGGGTCAAATCG-3' [SEQ ID NO: 2] (nucleotide positions 1295–1315); the products were analyzed on 1% agarose. An 1184 bp fragment was obtained from both samples containing transfectant viruses (lanes 5 and 6), but not from the Vero cells (lane 4) or the controls in which reverse transcriptase was omitted from the reaction (lanes 1–3). Purified RT-PCR fragments, derived from the transfectant viruses, were digested with Nhe I and Spe I restriction enzymes, as indicated (lanes 7–10). Only the DNA fragment derived from the tagged virus was able to be digested, thus verifying the presence of these two restriction sites (lanes 8 and 10), whereas the one derived from the control transfectant virus remains undigested (lanes 7 and 9). Lambda DNA, digested with Hind III/EcoR I, was used as a marker (lane M).
Figures 9A, 9B:
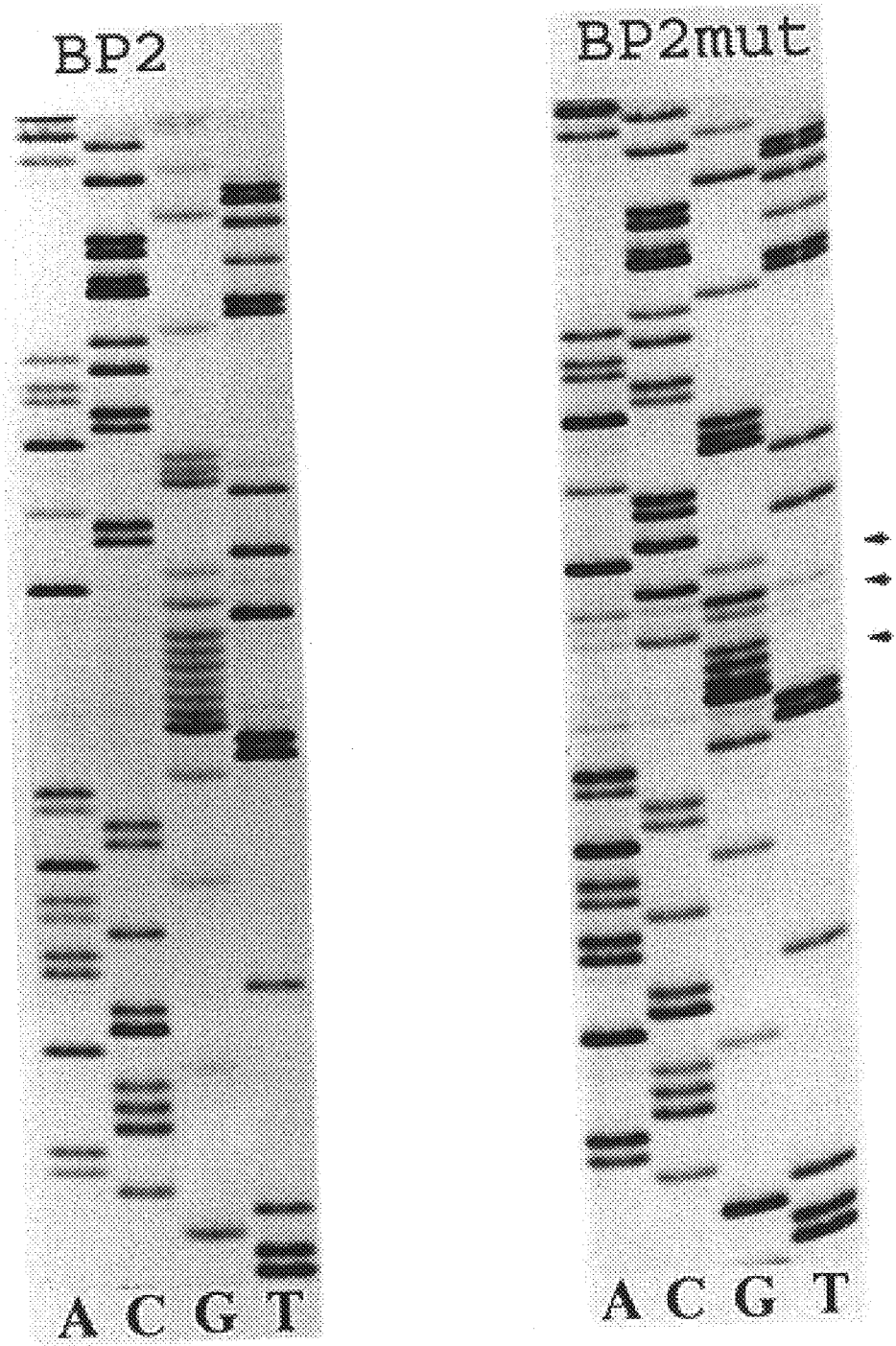
FIG. 9 is an autoradiogram showing the nucleotide sequences of cloned RT-PCR fragments from segment B of the unmodifed (BP2) and modified (BP2mut) transfectant viruses. Silent mutations at nucleotide positions 1770 (G→C), 1773 (T→C), and 1776 (G→C) are indicated by arrows.

Construction of Full-Length cDNA Clones of IBDV Genome. Full-length cDNA clones of IBDV segments A and B were independently prepared. The cDNA clones containing the entire coding region of the RNA segment A of strain D78 were prepared using standard cloning procedures and methods previously described (Vakharia, V. N., et al., (1994) Virus Res. 31, 265–273). To construct a full-length cDNA clone of segment A, two primer pairs (A5'-D78, A5-IPD78 and A3'D78, A3-IPD78) were synthesized and used for PCR amplification (see Table 4). The DNA segments were amplified according to the protocol of the supplier (New England Biolabs.) using DeepVent polymerase. Amplified fragments were cloned into the EcoR I site of a pCRII vector (Invitrogen Corp.) to obtain plasmids pCRD78A5' and pCRD78A3'. Each plasmid was digested with EcoR I and Sal 1, and the resultant fragments were ligated into EcoR I digested pUC19, to obtain plasmid pUC19FLAD78. This plasmid contains a full-length cDNA copy of segment A, which encodes all the structural proteins (VP2, VP4 and VP3), as well as the non-structural protein VP5 (see FIG. 6).

To obtain cDNA clones of segment B of P2 strain, two primer pairs (B5'-P2, B5-IPP2 and B3'-P2, B3-IPP2) were designed according to published sequences and used for RT-PCR amplification (see Table 4). Using genomic dsRNA as template, cDNA fragments were synthesized and amplified according to the supplier's protocol (Perkin-Elmer). Amplified fragments were blunt-end ligated into Sma I cleaved pBS vector (Stratagene) to obtain clones pBSP2B5' and pBSP2B3'. To construct a full-length clone of segment B, the 52-end fragment of plasmid pBSP2B5' was first subcloned between EcoR I and Pst I sites of pUC18 vector to obtain pUCP2B5'. Then the 3'-end fragment of plasmid pBSP2B3' was inserted between the unique Bgl II and Pst I sites of plasmid pUCP2B5' to obtain a full-length plasmid pUC18FLBP2, which encodes VP1 protein (see FIG. 6). Plasmids pUC18FLBP2 and pUC19FLAD78 were completely sequenced by using the sequenase DNA sequencing system (U.S. Biochem.), and the sequence data was analyzed using either DNASIS (Pharmacia) or PC/Gene (Intelligenetics) software. The integrity of the full-length constructs were tested by in vitro transcription and translation coupled reticulocyte lysate system using T7 RNA polymerase (Promega).

To introduce the sequence tags into segments A and B of IBDV, plasmids pUC19FLAD78mut and pUC18FLBP2mut were constructed by oligonucleotide-directed mutagenesis, using specific primer pairs and PCR amplification of their respective cDNA templates. To construct plasmid pUC19FLAD78mut, three primer pairs [RsrIIF, NheΔ(−); NheΔ(+), SpeΔ(−); and SpeΔ(+), SacIIR; see Table 4] were used in order to amplify the DNA fragments of 428, 655 and 623 base pairs (bp), respectively. These fragments were combined and subsequently reamplified by PCR using the flanking primers (RsrIIF and SacIIR) to produce a 1706 bp fragment. This fragment was cloned into a pCRII vector to obtain plasmid pCRNhe-Spe. This plasmid was digested with Rsr II and Sac II enzymes, and the resulting 1557 bp fragment was subcloned into unique Rsr II and Sac II sites of plasmid pUC19FLAD78. Finally, a mutant plasmid of segment A was obtained which contains the unique Nhe I and Spe I restriction sites (nucleotide positions 545 and 1180, respectively). Similarly, plasmid pUC18FLBP2 was modified by PCR using an oligonucleotide primer containing three silent mutations. After amplification, the resulting fragment was digested with Kpn I and Bgl II and cloned into Kpn 1-Bgl 11 cleaved pUC18FLBP2. A mutant plasmid of segment B (pUC18FLBP2mut) was obtained which contains the sequence tag (mutations at nucleotide positions 1770, 1773 and 1776).

Transcription and Transfection of Synthetic RNAs.

Plasmids pUC19FLAD78, pUC18FLBP2, and their mutant cDNA clones, were digested with BsrG I and Pst I enzymes (see FIG. 4), respectively, and used as templates for in vitro transcription with T7 RNA polymerase (Promega). Briefly, restriction enzyme cleavage assays were adjusted to 0.5% SDS and incubated with proteinase K (0.5 mg/ml) for 1 hr at 37° C. The linearized DNA templates (~3 pg) were recovered after ethanol precipitation, and were added separately to a transcription reaction mixture (50 μl) containing 40 mM Tris-HCl (pH 7.9), 10 mM NaCl, 6 mM $MgCl_2$, 2 mM spermidine, 0.5 mM ATP, CTP and UTP each, 0.1 mM GTP, 0.25 mM cap analog [m7G(5')ppp(5')G], 120 units of RNasin, 150 units T7 RNA polymerase (Promega), and incubated at 37° C. for 1 hr. Synthetic RNA transcripts were purified by phenol/chloroform extraction and ethanol precipitation. As controls, the transcription products were treated with either DNase or RNase (Promega) before the purification step.

Vero cells were grown to 80% confluency in 60 mm dishes and washed once with phosphate-buffered saline (PBS). Three ml of OPTI-MEM I (GIBCO/BRL) were added to the monolayers, and the cells were incubated at 37° C. for 1 hr in a $CO_2$ incubator. Simultaneously, 0.15 ml of OPTI-MEM I was incubated with 12.5 μg of Lipofectin reagent (GIBCO/BRL) for 45 min in a polystyrene tube at room temperature. Synthetic RNA transcripts of both segments resuspended in 0.15 ml of diethyl pyrocarbonate-treated water, were added to the OPTI-MEM-Lipofectin-mixture, mixed gently, and incubated on ice for 5 min. After removing the OPTI-MEM from the monolayers in 60 mm dishes and replacing with fresh 1.5 ml of OPTI-MEM, the nucleic acid containing mixture was added drop-wise to the Vero cells and swirled gently. After 2 hr of incubation at 37° C., the mixture was replaced with M199 medium containing 5% FCS (without rinsing the cells), and the cells were further incubated at 37° C. for desired time intervals.

Identification of Generated IBDV.

CEF cells were infected with the supernatant from Vero cells transfected with transcripts of either pUC19FLAD78, pUC18FLBP2 and/or their mutant plasmids. About 16 hrs post-infection, the whole cell nucleic acids were isolated as described (Mundt, E. & Müller, H. (1995) Virology 209, 10–18). Specific primers of segment A and B were used for RT of genomic RNA derived from these transfectant viruses.

Following RT, the reaction products were amplified by PCR using specific primer pairs of segment A and B. Resulting PCR fragments were either cloned and sequenced as described before, or digested with appropriate restriction enzymes to identify the tagged sequences.

Immunofluorescence.

Vero cells, grown on cover slips to 80% confluency, were infected with the supernatants derived from transfected Vero cells (after freeze-thawing) and incubated at 37° C. for two days. The cells were then washed, fixed with acetone, and treated with polyclonal rabbit anti-IBDV serum. After washing, the cells were treated with fluorescein labeled goat-anti-rabbit antibody (Kirkegaard & Perry Lab.) and examined by fluorescence microscopy.

Plaque Assay.

Monolayers of secondary CEF cells, grown in 60 mm dishes, were inoculated with the supernatants derived from transfected Vero cells. One hour post-infection, the cells were washed once with PBS, and overlayed with 0.8% noble Agar (Difco) containing 10% tryptose phosphate broth, 2% FCS, 0.112% $NaHCO_3$, 103 units penicillin, 103 µg/ml streptomycin, 0.25 µg/ml fungizone, 0.005% neutral red, and 0.0015% phenol red. The cells were incubated at 37° C. for 2 to 3 days until plaques could be observed and counted (Müller, H., Lange, H. & Becht, H. (1986) *Virus Res.* 4, 297–309).

Example 2
Generation of a Nonstructural Protein Deficient Mutant
Cells and Viruses.

Vero cells, used for transfection experiment, were maintained in M199 medium supplemented with 5% fetal bovine serum (FBS) at 37° C. in a humidified 5% $CO_2$ incubator. Primary chicken embryo fibroblast (CEF) cells were prepared as described (Mundt E., Vakharia V. N., 1996, Proc. Natl. Acad. Sci. USA 93, 11131–11136). Secondary CEF cells, used for virus titration, virus neutralization, immunofluorescence, and apoptosis assay, were maintained in growth medium consisting of M199 and F10 (50%/50% v/v) and 5% FBS. D78 strain of IBDV (Intervet Inc., Millsboro, Del.) and its transcripts-derived viruses were plaque purified twice, propagated and titrated in secondary CEF cells as described (Mundt E., Vakharia V. N., 1996, Proc. Natl. Acad. Sci. USA 93, 11131–11136). Virus stocks were established by serial passage of the recovered viruses in CEF cells, at a multiplicity of infection (MOI) of 0.01.

Construction of Full-Length cDNA Clones.

Figure 1:
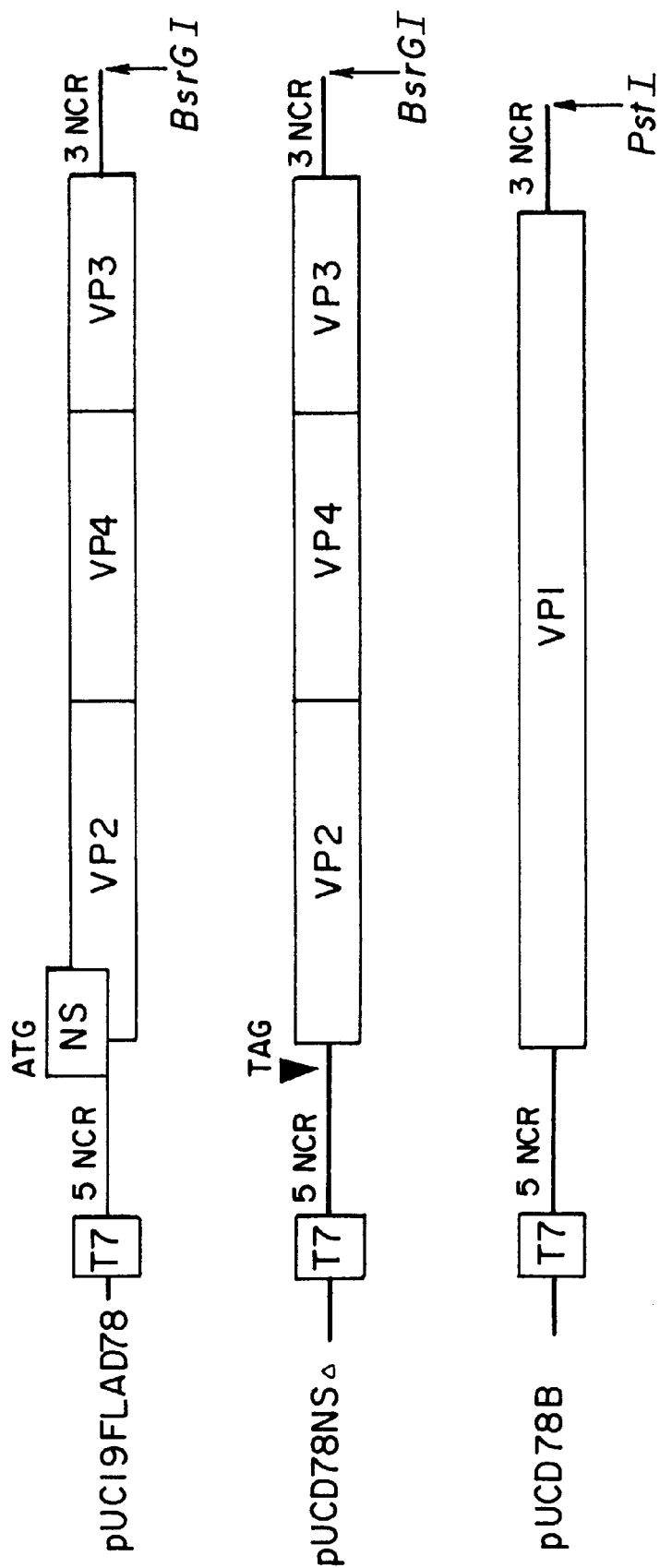
FIG. 1 shows a schematic presentation of IBDV cDNA constructs for the generation of plus-sense RNA transcripts with T7 RNA polymerase. Plasmid pUC19FLAD78 encodes the polyprotein (VP2-VP4-VP2) and the nonstructural protein (NS) of D78-IBDV. In plasmid pUCD78NSΔ, the initiation codon of NS gene is mutated to a stop codon. Plasmid pUCD78B encodes the RNA-dependent RNA polymerase (VP1). All plasmids contain a T7 promoter sequence at their 5'-end. Plasmids were linearized with the appropriate restriction enzymes as indicated(↑).
Figure 3A:
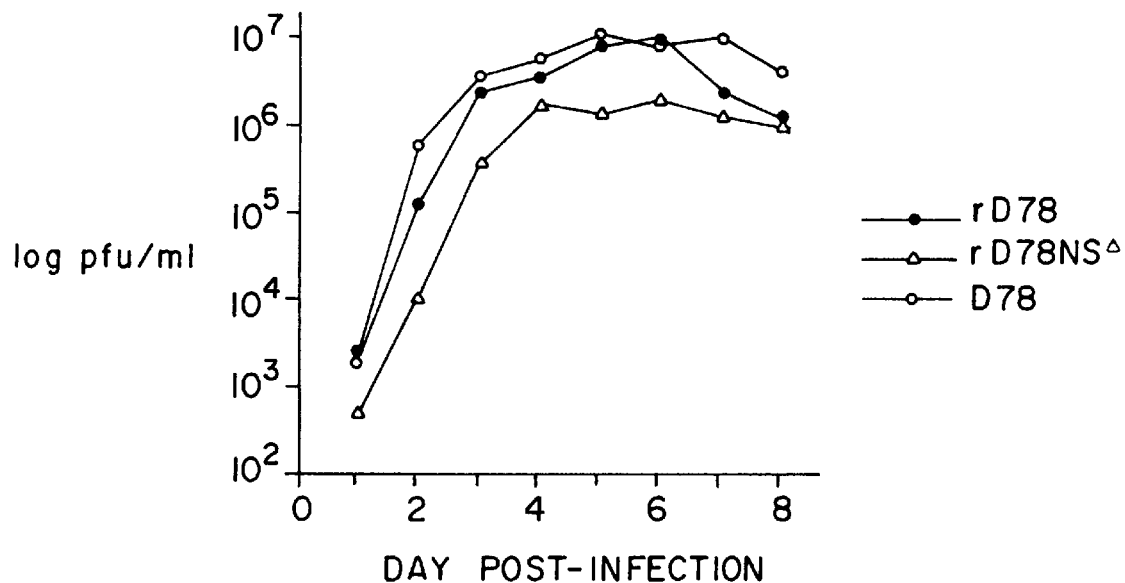
FIG. 3 shows the growth curve of IBDV (A) and cytotoxic effect (B) of IBDV infected cells. (A) Monolayers of chicken embryo fibroblast (CEF) cells were infected with equivalent amounts of indicated amounts of viruses at an multiplicity of infection (MOI) of 0.1, harvested at indicated time points, and infectious titers were determined by plaque assay. (B) Cell cultures were assayed for viability at the indicated time by trypan blue exclusion. Each value is the average of two independent experiments. ●, D78 wild type virus; ○, rD78 virus; ▲, rD78NSΔ virus; □ control cells (mock infected).
Figure 3B:
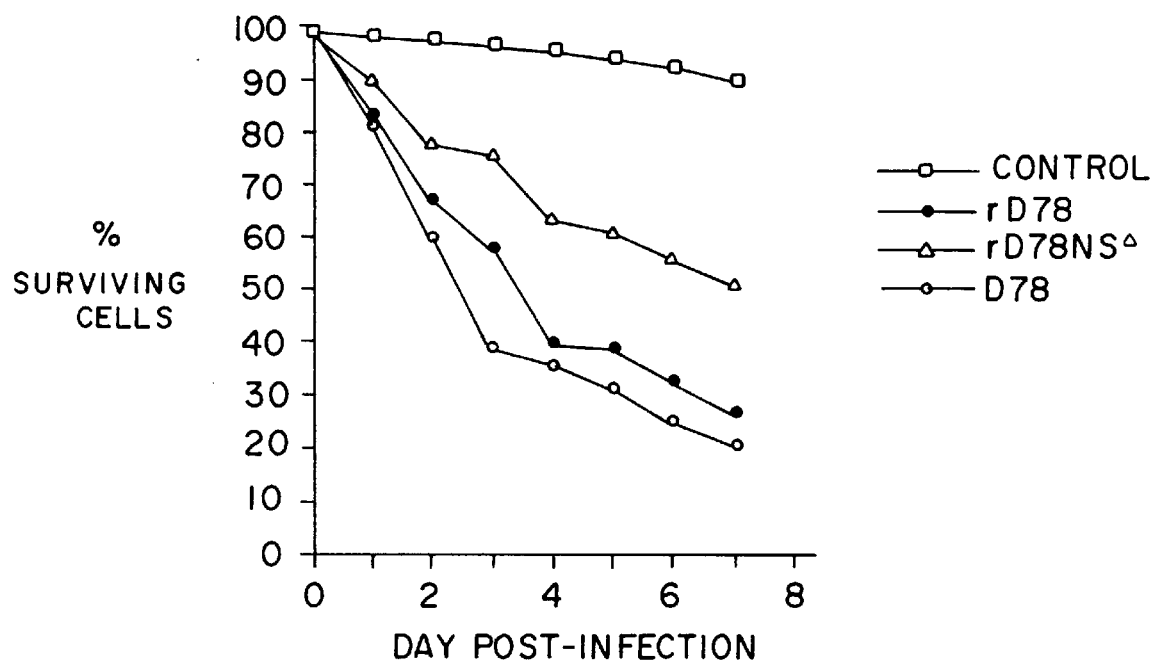
Figure 4A:
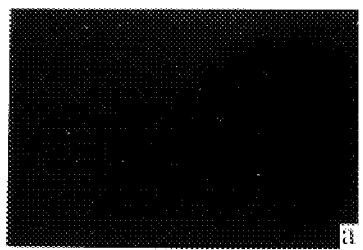
FIG. 4 shows an analysis of IBDV induced apoptosis by Terminal deoxynucleotide transferase-dUTP Nick-End-Labeling (TUNEL) assay. Chicken embryo fibroblast (CEF) cells were either mock-infected (a, d, g) or infected with mutant rD78NSΔ (b, e, h) or recombinant rD78 (c, f, i) IBDV at an multiplicity of infection (MOI) of 1. Cells were fixed at 24 h (a, b, c), 48 h (d, e, f), 72 h (g, h, i) post-infection, and assayed by immunofluorescence for DNA breakage (TdT assay, green signal). The TUNEL staining of chicken embryo fibroblast (CEF) cells infected with NS protein-deficient mutant IBDV show a significant reduction in IBDV-induced apoptosis. (Magnifications are ×100).
Figure 4B:
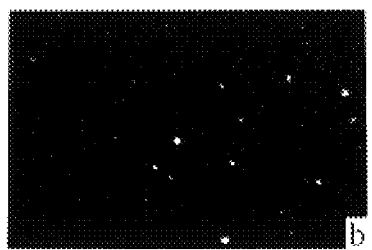
Figure 4C:
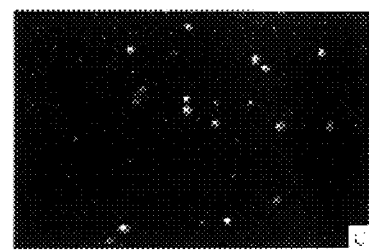
Figure 4D:
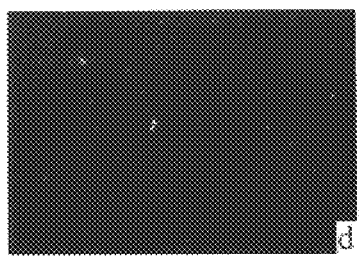
Figure 4E:
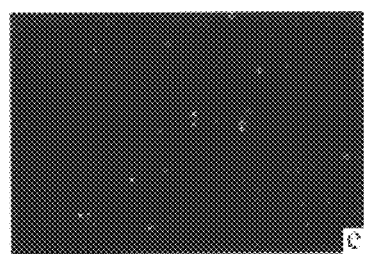
Figure 4F:
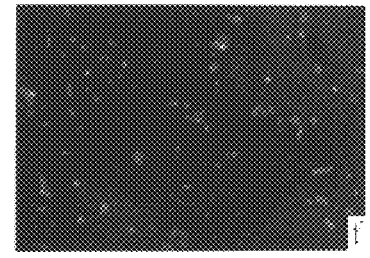
Figure 4G:
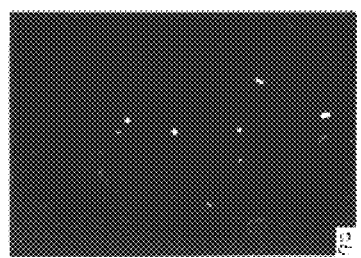
Figure 4H:
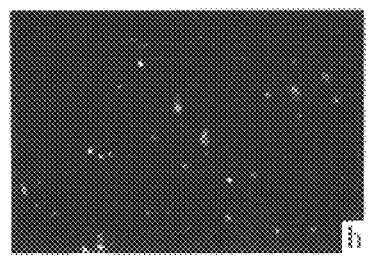
Figure 4I:
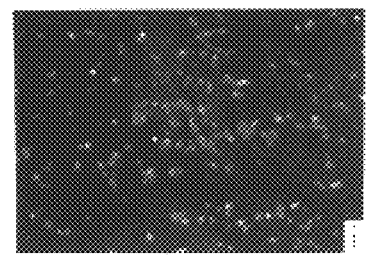
Figure 5A:
FIG. 5 shows the histopathologic appearance of sections (hematoxylin and eosin) of bursa of Fabricius from uninfected and infected chickens. (a) Cortical lymphocytes (dark gray cells adjacent to connective tissue that separates follicles) and medullary lymphocytes (light gray cells in follicle centers) in portions of 6 follicles from an uninfected chicken are normal. In addition, the interfollicular connective tissues are normal. (b) Follicles and interfollicular connective tissues from a chicken infected with the mutant rD78NSΔ virus are normal and can not be differentiated from their control counterparts. (c) There is lymphocyte necrosis and heterophilic inflammation in 6 follicles in the bursa of Fabricius from a chicken infected with rD78 virus. Notice the loss of distinction between the cortex and the medulla, and the bands of interfollicular connective tissue that are infiltrated by myriad heterophils and macrophages. (Magnifications are ×100).
Figure 5B:
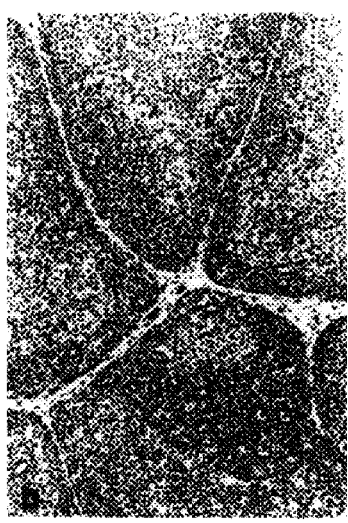
Figure 5C:
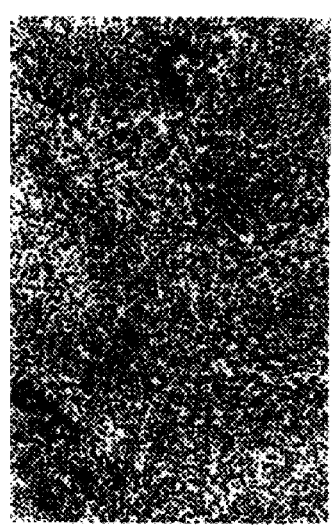

All manipulations of DNAs were performed according to standard protocols (Sambrook, J., et al., 1989, Molecular Cloning: A Laboratory Manual, 2nd ed. Cold Spring Harbor Laboratory, Cold Spring Harbor, N.Y.). Construction of a full-length cDNA clone of IBDV genome segment A of strain D78 has been described previously (Mundt E., Vakharia V. N., 1996, Proc. Natl. Acad. Sci. USA 93, 11131–11136). It encodes all of the structural proteins (VP2, VP4, and VP3), as well as the NS protein (FIG. 1). To construct a mutant cDNA clone of segment A lacking the initiation codon of the NS gene, two primer pairs (pUCNde+, NSΔ−; and NSΔ+, NdeBV) were synthesized and used for PCR amplification of the parent plasmid pUC19FLAD78. These primer pairs, pUCNde+(5'-CCATATGCGGTGTGAAATACCG-3' [SEQ ID NO: 3], nucleotide positions 482–503 in pUC19), NS(-(5'-CTCTACTAACCTACAATGATAGCG-3' [SEQ ID NO: 4], positions 86–109 of IBDV segment A), and NS(+(5'-CGCTATCATTGTAGGTTAGTAGAG-3' [SEQ ID NO: 5]), NdeBV (5'-CATACCCAAGATCATATGATGTG-3' [SEQ ID NO: 6], positions 640–662 of segment A), yielded DNA fragments of 342 and 576 base pairs (bp), respectively. These fragments were combined and subsequently amplified by PCR, using the flanking primers (pUCNde+ and NdeBV) to produce a 918-bp fragment. This fragment was cloned into a pCRII vector (Invitrogen Corp.) to obtain plasmid pCRNSΔ. This plasmid was digested with Nde I enzyme, and the resulting fragment was inserted into Nde I-cleaved plasmid pUC19FLAD78. Finally, a mutant clone of segment A (pUCD78NSΔ) was obtained in which the ATG of NS gene (positions 97 and 98) was mutated to TAG (FIG. 1).

To construct a cDNA clone of segment B of homologous IBDV strain D78, two primer pairs (B5'-D78, B5-IPD78 and B3'-D78, B3-IPD78) were synthesized and used for reverse transcription (RT)-PCR amplification. Sequences of the primers were identical to the one used for the construction of segment B cDNA clone of P2 strain (Mundt E., Vakharia V. N., 1996, Proc. Natl. Acad. Sci. USA 93, 11131–11136). Using genomic dsRNA as a template, cDNA fragments were synthesized and amplified according to the suppliers protocol (Perkin-Elmer). Amplified fragments were cloned between the EcoR I site of a pCRII vector to obtain plasmids pCRD78A5' and pCRD78A3'. To construct a full-length clone of segment B, the 5'-end fragment of IBDV (from plasmid pCRD78B5') was first subcloned between EcoR I and Pst I sites of pUC19 vector to obtain pUCD785'. Then the 3'-end fragment of IBDV (from plasmid pCRD78B3') was inserted between the unique Bgl II and Pst I sites of plasmid pUCD78B5' to obtain a full-length plasmid pUCD78B, which encodes VP1 protein (FIG. 1).

DNA of plasmid pUCD78NSΔ and pUCD78B was sequenced by dideoxy chain termination method (Sanger, F., et al., 1977, Proc. Natl. Acad. Sci. USA, 74: 5463–5467) using an Automated DNA Sequencer (Applied Biosystem), and the sequence data was analyzed using PC/Gene (Intelligenetics) software. The integrity of the full-length constructs was tested by in vitro transcription and translation coupled reticulocyte lysate system using T7 RNA polymerase (Promega Corp.).

Transcription, and Transfection of Synthetic RNAs.

Transcription and transfection assays were performed as described in detail previously (Mundt E., Vakharia V. N., 1996,Proc. Natl. Acad. Sci. USA 93,11131–11136). Briefly, plasmids pUC19FLAD78, pUCD78NSΔ and pUCD78B were digested with BsrG I and Pst I enzymes (FIG. 1), respectively, and used as templates for in vitro transcription with T7 RNA polymerase (Promega Corp.). Vero cells were transfected with combined transcripts of either mutant or the wild-type segment A, and segment B, using Lipofectin reagent (GIBCO/BRL). The resulting virus progeny was designated as IBDV rD78NSΔ and rD78, respectively.

Characterization of Transcript-Derived IBDV In Vitro.

Transcript-derived or transfectant viruses were characterized by immunofluorescence assay (IFA) using rabbit anti-IBDV polyclonal or rabbit anti-NS specific serum as described before (Mundt E., Vakharia V. N., 1996, Proc. Natl. Acad. Sci. USA 93, 11131–11136). Briefly, CEF cells were infected with rD78 or rD78NSΔ IBDV at an multiplicity of infection (MOI) of 1, and incubated at 37° C. for an appropriate time interval. The cells were then washed with phosphate-buffered saline, pH 7.4 (PBS), fixed with ice-cold methanol-acetone (1:1), and treated with either rabbit anti-NS specific serum or rabbit anti-IBDV serum. After washing with PBS, the cells were treated with fluorescein labeled goat-anti-rabbit antibody (Kirkegaard & Perry Laboratories) and examined by fluorescence microscopy. To examine viral structural proteins expressed by transfectant viruses, rD78 and rD78NSΔ IBDV were purified by sucrose and CsCl gradient centrifugation as described (Nick, H., et al., 1976, J. Virol. 18:227–234), and were adjusted to a protein concentration of 0.1 mg/mi. Equivalent amounts of purified viral samples were fractionated on a 12.5% SDS-polyacrylamide gel, transferred onto nitrocellulose membrane, reacted with rabbit anti-IBDV serum, and detected with streptavidin-alkaline phosphatase and naphthol phosphate fast red color development reagents (Vakharia, V. N., et al., 1993, J. Gen. Virol. 74, 1201–1206).

Growth Curve of IBDV.

To analyze the growth characteristics of IBDV, confluent secondary CEF cells (in T-25 flasks) were infected with the parental D78 or with transcript-derived rD78 or rD78NSΔ virus stocks (generated after five passages in CEF cells) at an multiplicity of infection (MOI) of 0.1. Infected cell cultures were harvested at different time intervals and the titer of infectious virus present in the culture was determined by plaque assay on CEF cells, as described (Mundt E., et al., 1996, Proc. Natl. Acad. Sci. USA 93, 11131–11136).

Assays for Cell Viability and Apoptosis.

For cell viability assay, secondary CEF cells were grown to 80% confluence in T-25 flask and infected with D78, rD78 or rD78NSΔ IBDV at an multiplicity of infection (MOI) of 1. Cell viability was measured by trypan blue exclusion or by calorimetric MTT (tetrazolium) assay (Mosmann, T., 1983, J. Immuno. Methods 65:1170–1174). To study apoptosis, secondary CEF cells (grown on cover slips to 80% confluence) were either mock-infected or infected the transfectant viruses at an multiplicity of infection (MOI) of 1, and analyzed by Terminal deoxynucleotide transferase-dUTP Nick-End-Labeling (TUNEL) assay. Apoptosis was monitored at 24, 48 and 72 h post-infection by using the terminal deoxynucleotidyl transferase (TdT) based In Situ Cell Death Detection kit (Boehringer Mannheim Corp.), which measures the DNA strand breakage. Briefly, infected CEF cells (on cover slips) were washed with PBS, and fixed with freshly made 4% formaldehyde in PBS for 30 min at room temperature. The fixed cells were rinsed three times with PBS and then placed (upside down) in a dish containing 50 µl of TdT labeling mix (1×TdT reaction buffer, 2.5 mM CoCl$_2$, 0.1 mM dithiothreitol, 0.25 U of TdT per ml, 10 mM fluorescein-16-dUTP). The reaction was carried out at 37° C. in a humidified incubator for 60 min. The cells were then rinsed with PBST (PBS with 0.1% Triton X-100 and 0.5% Tween 20) and examined by fluorescence microscopy.

Chicken Inoculation and Serology.

Three-week-old specific pathogen free (SPF) chickens were obtained (SPAFAS, Inc., Storrs, Conn.), and housed in isolators. Prior to inoculation, the chickens were bled and their sera tested by ELISA to make sure that they were negative for IBDV-specific antibodies. Three groups of SPF chickens (50 in each group) were given one of three treatments consisting of 2 drops of either culture medium (control), rD78 virus (5×103 PFU/ml), or rD78NSΔ virus (5×103 PFU/ml) into the conjunctival sac. Eight chickens from each group were removed at 2, 4, 6, 9, and 21 days post infection (DPI) and humanely killed by cerebrocervical separation. The bursa of Fabricius (BF) was excised from each chicken and bisected. One BF hemisection was stored at −70° C. and used for virus isolation and RT-PCR assay. The other BF hemisection was fixed and sectioned for histopathological examination and indirect immunofluorescence assay as described.

To evaluate the immune response of the mutant virus in vivo, blood samples were collected from each sampled chicken's ventral medial wing vein before necropsy at 14 and 21 DPI. Virus neutralizing (VN) antibody titer was determined using parental IBDV strain D78 on CEF cells, as described previously (Vakharia V. N., et al., 1994, Vaccine 12:452–456). The VN titer was reported as log$_2$ of the highest reciprocal dilution that was capable of neutralizing 500 PFU of D78 IBDV. In addition, the serum was assayed for reovirus, Newcastle disease virus, infectious laryngotracheitis virus, infectious bronchitis virus, and avian encephalomyelitis virus antibodies by using ELISA kits (Kirkegaard & Perry Laboratories).

Characterization of Recovered Viruses In Vivo.

To detect and isolate the viruses from the chickens inoculated with the transfectant viruses, the bursa from each sampled chicken was ground in PBS to make 10% bursal suspension. One-half ml bursal homogenate was mixed with 4.5 ml of Ml 99 medium and passed through 0.45 pm syringe filter. The filtrate was used to infect confluent monolayers of CEF cells in T-75 flask. The cells were examined daily (up to 5 days) for the presence or absence of IBDV-specific cytopathic effect. In addition, the titer of the virus present in these cultures was determined by plaque assays on CEF cells as described (Mundt E., et al., 1996, Proc. Natl. Acad. Sci. USA 93, 11131–11136).

Identification of Recovered Viruses by RT-PCR.

Total nucleic acids of uninfected and IBDV-infected CEF cells or bursal homogenates were isolated and analyzed by RT-PCR, respectively. RT-PCR reactions were performed essentially as described (Mundt E., et al., 1996, Proc. Natl. Acad. Sci. USA 93, 11131–11136). Specific NheΔ(−) primer of segment A (5'-CCCATTGTAGCATGCATCTGTCAG-3' [SEQ ID NO: 7], binding to nucleotide positions 536–559) was used for RT of genomic RNA. Following RT, the reaction products were amplified by PCR using an A5'-D78 specific primer of segment A (5'-GGATACGATCGGTCTGACCCCGGGGGAGTCA-3' [SEQ ID NO: 8], nucleotide positions 1–31). The reaction products were separated by one percent agarose gel electrophoresis, and purified by using QIAquick gel extraction kit (QIAGEN Inc.). The PCR fragment, comprising the NS gene and the 5'-noncoding region of segment A, was cloned into a pCRII vector, and sequenced as described before.

Histopathological Studies.

The BF tissues were fixed by immersion in 10% neutral buffered formalin. The ratio of fixative to BF exceeded 10:1. Seven days later, a cross-sectional portion of each BF was processed through paraffin, stained with haematoxylin and eosin, and examined with a light microscope. The severity of the lesion was graded on a scale of − to +++ based on the extent of lymphocyte necrosis, follicular depletion, and atrophy.

TABLE 1

Gross and microscopic lesions in the bursa of Fabricius from chickens infected with rD78 or rD78NSΔIBDV

| Days post-infection | Groups | Pathology gross[a] | microscopic[b] |
|---|---|---|---|
| 2 | control | − | − |
|   | rD78 | − | ++ (4/8) |
|   | rD78NSΔ | − | − |
| 4 | control | − | − |
|   | rD78 | − | +++ (6/8) |
|   | rD78NSΔ | − | − |
| 6 | control | − | − |
|   | rD78 | + | +++ (8/8) |
|   | rD78NSΔ | − | − |
| 9 | control | − | − |
|   | rD78 | + | +++ (7/8) |
|   | rD78NSΔ | − | − |
| 21 | control | − | − |
|   | rD78 | − | − |
|   | rD78NSΔ | − | − |

[a]+, small bursa: −, no gross lesion.
[b]+, multifocal purulent necrotizing bursitis with follicular depletion. −, no histological lesion. Numbers in parentheses represent number of bursa with lesions/number of bursa examined. The result is the representative of two independent experiments.

TABLE 2

Detection of virus in the bursa of chickens infected with rD78 or rD78NSΔIBDV[a]

| Group(s) | Isolation of virus on day: | | | | | RT-PCR on day: | | | | |
|---|---|---|---|---|---|---|---|---|---|---|
|   | 2 | 4 | 6 | 9 | 21 | 2 | 4 | 6 | 9 | 21 |
| control | − | − | − | − | − | − | − | − | − | − |
| rD78 | + | + | + | − | − | + | + | + | − | − |
| rD78NSΔ | + | + | + | + | − | + | + | + | + | − |

[a]+, virus detected by virus isolation, or by PT-PCR: −, no virus detected.

TABLE 3

Virus and virus-neutralizing antibody titers of chickens infected with rD78 or rD78NSΔ IBDV

| Group(s) | Virus titers[a] (PFU/ml) in bursa on day: | | | | | VN titer[b] ($\log_2$) on day: | |
|---|---|---|---|---|---|---|---|
|   | 2 | 4 | 6 | 9 | 21 | 14 | 21 |
| Control | 0 | 0 | 0 | 0 | 0 | ≦2 | ≦2 |
| rD78 | $7.2 \times 10^6$ | $2.3 \times 10^6$ | $1.3 \times 10^2$ | 0 | 0 | 11.3 ± 1.1 | 12.2 ± 0.4 |
| rD78NSΔ | $3.0 \times 10^5$ | $6.8 \times 10^5$ | $2.2 \times 10^6$ | $1.8 \times 10^2$ | 0 | 10.8 ± 0.5 | 12.0 ± 0.1 |

[a]Virus titers were determined by plaque assays on CEF cells.
[b]Virus neutralizations were performed on CEF cells, and the ability to neutralize 500 PFU of D78 wild-type virus is represented as log of the 50% endpoint titer.

TABLE 4

Oligonucleotides Used for the Construction of Full Length cDNA Clones of IBDV Genomic Segments of A and B.

| Nucleotide Sequence | Orientation | Name | Nucleotide Number |
|---|---|---|---|
| *TAATCGACTCACTATA*GGATACGATCGGTCTGACCCCGGGGAGTCA [SEQ ID NO: 9] | + | A5'-D78 | 1–31 |
| TGTACAGGGGACCCGCGAACGGATCCAATT [SEQ ID NO: 10] | − | A3'-D78 | 3237–3261 |
| CGTCGACTACGGGATTGTGG [SEQ ID NO: 11] | − | A5-IPD78 | 1711–1730 |
| AGTCGACGGGATTCTTGCTT [SEQ ID NO: 12] | + | A3-IPD78 | 1723–1742 |
| ATGACAAACCTGCAAGAT [SEQ ID NO: 13] | + | RsrIIF | 131–148 |
| CTGACAGATGCTAGCTACAATGGG [SEQ ID NO: 14] | + | NheΔ(+) | 536–559 |
| GTCCCGTCACACTAGTGGCCTA [SEQ ID NO: 15] | + | SpeΔ(+) | 1170–1191 |
| CCTCTCTTAACACGCAGTCG [SEQ ID NO: 16] | − | SacIIR | 1174–1793 |
| AGAGAATTCTAATACGACTCACTATA*GGATACGATGGGTCTGAC* [SEQ ID NO: 17] | + | B5'-P2 | 1–18 |

TABLE 4-continued

Oligonucleotides Used for the Construction of Full Length cDNA Clones of IBDV Genomic Segments of A and B.

| Nucleotide Sequence | Orientation | Name | Nucleotide Number |
|---|---|---|---|
| CGATCTGCTGCAGGGGGCCCCCGCAGGCGAAGG [SEQ ID NO: 18] | − | | 2807–2827 |
| CTTGAGACTCTTGTTCTCTACTCC [SEQ ID NO: 19] | − | B5-IPP2 | 1915–1938 |
| ATACAGCAAAGATCTCGGG [SEQ ID NO: 20] | + | B3-IPP2 | 1839–1857 |

Composition and location of the oligonucleotide primers used for cloning. T7 promoter sequences are marked with italic type, the virus specific sequences are underlined, and the restriction sites marked in boldface type. Orientation of the virus-specific sequence of the primer is shown for sense (+) and antisense (−). The positions where the primers bind (nucleotide number) are according to the published sequences of P2 strain.

TABLE 5

Generation of Infectious IBDV From Synthetic RNAs of Segment A and B.

| Material Transfected | CPE | Immunofluorescence |
|---|---|---|
| ssRNA A + B, DNase-treated | + | + |
| ssRNA A + B, RNase-treated | − | − |
| ssRNA A + B, untreated | + | + |
| ssRNA A, untreated | − | − |
| ssRNA B, untreated | − | − |
| Lipofectin only | − | − |

Vero cells were transfected with synthetic RNAs of segment A and B, derived from transcription reactions, that were either untreated or treated with DNase or RNase. After 5 days, the supernatants were collected, clarified by centrifugation, and analyzed for the presence of virus. The infectivity of the recovered virus was detected in CEF by the appearance of cytopathic effect (CPE) 1–2 days post-inoculation. The specificity of the recovered virus was determined by immunofluorescence staining of infected Vero cells with rabbit anti-IBDV serum.

TABLE 6

Recovery of Virus at Various Times Post-Transfection.

| Time in hours post-transfection | CPE | Immunofluorescence | pfu/ml |
|---|---|---|---|
| 4 | − | − | 0 |
| 8 | − | − | 0 |
| 16 | − | − | 0 |
| 24 | − | − | 0 |
| 36 | + | + | $2.3 \times 10^2$ |
| 48 | + | + | $6.0 \times 10^1$ |

Vero cells were transfected with synthetic RNAs of segment A and B as described. The infectivity and specificity of the recovered virus was detected by CPE in CEF and immunofluorescence staining in Vero cells, respectively. Monolayers of secondary CEF were used for plaque assay after inoculating the cells with the supernatants derived from transfected Vero cells. Approximate titer of the virus was calculated as plaque forming units per ml (pfu/ml).

What is claimed is:

1. A live, nonpathogenic infectious bursal disease virus, wherein said virus is NS protein deficient and wherein said NS protein is about 17 kDa in size.

2. A nonpathogenic, chimeric, infectious bursal disease virus, wherein said virus is NS protein deficient and contains epitopic determinants from at least two different infectious bursal disease virus strains, and wherein said NS protein is about 17 kDa in size.

3. The virus according to claim 2, wherein said infectious bursal disease virus strains are selected from the group consisting of D78, E/Del and GLS.

4. A vaccine comprising the nonpathogenic, chimeric, infectious bursal disease virus according to claim 2, in combination with a pharmaceutically acceptable carrier.

5. A live infectious, chimeric, nonpathogenic infectious bursal disease virus, wherein said virus is made by a process comprising the steps of
preparing cDNA containing infectious bursal disease virus genome segments A and B, wherein segment A is modified to prevent the expression of an NS protein which is about 17 kDa, and said cDNA encodes epitopic determinants from at least two different infectious bursal disease virus strains,
transcribing said cDNA to produce synthetic RNA transcript,
transfecting a host cell with said synthetic RNA transcript,
incubating said host cell in a culture medium, and
isolating live, nonpathogenic infectious bursal disease virus from said culture medium.

6. A vaccine comprising an infectious, nonpathogenic infectious bursal disease virus according to claim 5 in combination with a pharmaceutically acceptable carrier.

7. A method for preparing nonpathogenic, infectious bursal disease virus, wherein said infectious bursal disease virus naturally produces a NS protein which is about 17 kDa, comprising the following steps:
preparing cDNA containing infectious bursal disease virus genome segments A and B, wherein the cDNA of segment A is modified to prevent the expression of an NS protein which is about 17 kDa,
transcribing said cDNA to produce synthetic RNA transcripts,
transfecting host cells with said synthetic RNA transcripts,
incubating said host cells in a culture medium, and
isolating live, nonpathogenic infectious bursal disease virus from said culture medium.

8. The method according to claim 7, wherein said host cells are African green monkey Vero cells or chicken embryo fibroblast cells.

9. The method according to claim 7, wherein said cDNA is prepared from more than one strain of infectious bursal disease virus.

10. The method according to claim 9, wherein said segment A is present in plasmid pUCD78NSΔ.

11. The method according to claim 9, wherein said segment B is present in plasmid pUCD78B.

12. The method according to claim 7, wherein the cDNA for segment A is modified by mutating the initiation codon of the NS gene to a stop codon.

13. A method for producing a live infectious bursal disease virus vaccine, comprising the steps of
preparing full-length cDNA containing infectious bursal disease virus genome segments A and B, wherein segment A has been modified to prevent expression of an NS protein which is 17 kDa in size,
transcribing said cDNA to produce synthetic RNA transcripts,
purifying said synthetic RNA transcripts,
transfecting host cells with said purified RNA transcripts,
incubating said host cells in a culture medium,
isolating live infectious, nonpathogenic infectious bursal disease virus from said culture medium, and
combining said live infectious, nonpathogenic infectious bursal disease virus with a pharmaceutically acceptable carrier to produce a live, nonpathogenic infectious bursal disease virus vaccine.

14. A method for generating a nonpathogenic, chimeric infectious bursal disease virus, comprising the following steps:
preparing cDNA containing infectious bursal disease virus genome segments A and B, wherein the cDNA of segment A is modified to prevent the expression of an NS protein which is about 17 kDa and said cDNA of segment A encodes epitopic determinants from at least two different infectious bursal disease virus strains, transcribing said cDNA to produce synthetic RNA transcripts, transfecting host cells with said synthetic RNA transcripts, incubating said host cells in a culture medium, and isolating live, nonpathogenic, chimeric, infectious bursal disease virus from said culture medium.

15. Synthetic RNAs encoding proteins VP1, VP2, VP3, and VP4 of infectious bursal disease virus, wherein said RNAs do not express NS protein.

16. A host cell transfected with the synthetic RNA according to claim 15.

17. A cDNA or set of cDNAs containing at least a portion of the infectious bursal disease virus genome selected from the group consisting of segment A, and segments A and B of infectious bursal disease virus, wherein said cDNA includes the 5' and 3' termini of said segments and wherein segment A is modified to prevent expression of an NS protein which is about 17 kDa.

18. A recombinant vector or set of vectors comprising the cDNA according to claim 17.

19. The vector or set of vectors according to claim 18, wherein each vector is a plasmid.

20. A host cell transformed with the vector(s) according to claim 19.

* * * * *

UNITED STATES PATENT AND TRADEMARK OFFICE
CERTIFICATE OF CORRECTION

PATENT NO.     : 6,231,172 B1
DATED          : May 15, 2001
INVENTOR(S)    : Noribumi Koitabashi et al.

It is certified that error appears in the above-identified patent and that said Letters Patent is hereby corrected as shown below:

Title page,
Item [56], References Cited, FOREIGN PATENT DOCUMENTS, insert -- 2-39213 1/1982 (JP) --; and "57-73623  10/1980 (JP)" should read -- 57-73623  5/1980 (JP) --.

Column 4,
Line 16, "FIG. 24A" should read -- FIGS. 24A --.

Column 11,
Line 15, "AP." should read -- $\Delta P$. --.

Column 14,
Line 1, "tot he" should read -- to the --.
Line 9, "AP" should read -- $\Delta P$ --.
Line 25, "AP" should read -- $\Delta P$ --.

Column 15,
Line 15, "AP" should read -- $\Delta P$ --.

Column 23,
Line 40, "Pi" should read -- P1 --.
Line 63, "PS," should read -- P5, --.
Line 65, "P2<PS," should read -- P2<P5, --.

Column 24,
Line 17, "can not" should read -- cannot --.
Line 25, "and" should read -- end --.

Column 27,
Line 22, "be also" should read -- also be --.
Line 65, "3008" should read -- 3004 --.

UNITED STATES PATENT AND TRADEMARK OFFICE
CERTIFICATE OF CORRECTION

PATENT NO. : 6,231,172 B1
DATED : May 15, 2001
INVENTOR(S) : Noribumi Koitabashi et al.

It is certified that error appears in the above-identified patent and that said Letters Patent is hereby corrected as shown below:

Column 35,
Line 63, "dyne/cm))," should read -- dyne/cm), --.

Column 42,
Line 43, "as" should read -- as a --.

Signed and Sealed this

Twenty-fifth Day of June, 2002

Attest:

JAMES E. ROGAN
Attesting Officer
Director of the United States Patent and Trademark Office

SEQUENCE LISTING

<160> NUMBER OF SEQ ID NOS: 25

<210> SEQ ID NO: 1
<211> LENGTH: 18
<212> TYPE: DNA
<213> ORGANISM: Artificial Sequence
<220> FEATURE:
<223> OTHER INFORMATION: Description of Artificial Sequence: PRIMER

<400> SEQUENCE: 1
atgacaaacc tgcaagat                                                18

<210> SEQ ID NO: 2
<211> LENGTH: 21
<212> TYPE: DNA
<213> ORGANISM: Artificial Sequence
<220> FEATURE:
<223> OTHER INFORMATION: Description of Artificial Sequence: PRIMER

<400> SEQUENCE: 2
catggctcct gggtcaaatc g                                            21

```
<210> SEQ ID NO: 3
<211> LENGTH: 22
<212> TYPE: DNA
<213> ORGANISM: Artificial Sequence
<220> FEATURE:
<223> OTHER INFORMATION: Description of Artificial Sequence: PRIMER

<400> SEQUENCE: 3
ccatatgcgg tgtgaaatac cg                                                 22

<210> SEQ ID NO: 4
<211> LENGTH: 24
<212> TYPE: DNA
<213> ORGANISM: Artificial Sequence
<220> FEATURE:
<223> OTHER INFORMATION: Description of Artificial Sequence: PRIMER

<400> SEQUENCE: 4
ctctactaac ctacaatgat agcg                                               24

<210> SEQ ID NO: 5
<211> LENGTH: 24
<212> TYPE: DNA
<213> ORGANISM: Artificial Sequence
<220> FEATURE:
<223> OTHER INFORMATION: Description of Artificial Sequence: PRIMER

<400> SEQUENCE: 5
cgctatcatt gtaggttagt agag                                               24

<210> SEQ ID NO: 6
<211> LENGTH: 23
<212> TYPE: DNA
<213> ORGANISM: Artificial Sequence
<220> FEATURE:
<223> OTHER INFORMATION: Description of Artificial Sequence: PRIMER

<400> SEQUENCE: 6
catacccaag atcatatgat gtg                                                23

<210> SEQ ID NO: 7
<211> LENGTH: 24
<212> TYPE: DNA
<213> ORGANISM: Artificial Sequence
<220> FEATURE:
<223> OTHER INFORMATION: Description of Artificial Sequence: PRIMER

<400> SEQUENCE: 7
cccattgtag catgcatctg tcag                                               24

<210> SEQ ID NO: 8
<211> LENGTH: 31
<212> TYPE: DNA
<213> ORGANISM: Artificial Sequence
<220> FEATURE:
<223> OTHER INFORMATION: Description of Artificial Sequence: PRIMER

<400> SEQUENCE: 8
ggatacgatc ggtctgaccc cgggggagtc a                                       31

<210> SEQ ID NO: 9
<211> LENGTH: 48
<212> TYPE: DNA
<213> ORGANISM: Artificial Sequence
<220> FEATURE:
<223> OTHER INFORMATION: Description of Artificial Sequence:
```

OLIGONUCLEOTIDE

<400> SEQUENCE: 9
taatacgact cactatagga tacgatcggt ctgaccccgg gggagtca                48

<210> SEQ ID NO: 10
<211> LENGTH: 30
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 10
tgtacagggg acccgcgaac ggatccaatt                                    30

<210> SEQ ID NO: 11
<211> LENGTH: 20
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 11
cgtcgactac gggattctgg                                               20

<210> SEQ ID NO: 12
<211> LENGTH: 20
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 12
agtcgacggg attcttgctt                                               20

<210> SEQ ID NO: 13
<211> LENGTH: 18
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 13
atgacaaacc tgcaagat                                                 18

<210> SEQ ID NO: 14
<211> LENGTH: 24
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 14
ctgacagatg ctagctacaa tggg                                          24

<210> SEQ ID NO: 15
<211> LENGTH: 22
<212> TYPE: DNA
<213> ORGANISM: Artificial Sequence
<220> FEATURE:
<223> OTHER INFORMATION: Description of Artificial Sequence:
      OLIGONUCLEOTIDE

```
<400> SEQUENCE: 15
gtcccgtcac actagtggcc ta                                         22

<210> SEQ ID NO: 16
<211> LENGTH: 20
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 16
cctctcttaa cacgcagtcg                                            20

<210> SEQ ID NO: 17
<211> LENGTH: 44
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 17
agagaattct aatacgactc actataggat acgatgggtc tgac                 44

<210> SEQ ID NO: 18
<211> LENGTH: 33
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 18
cgatctgctg caggggggccc ccgcaggcga agg                            33

<210> SEQ ID NO: 19
<211> LENGTH: 24
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 19
cttgagactc ttgttctcta ctcc                                       24

<210> SEQ ID NO: 20
<211> LENGTH: 19
<212> TYPE: DNA
<213> ORGANISM: Artificial Sequence
<220> FEATURE:
<223> OTHER INFORMATION: Description of Artificial Sequence:
      OLIGONUCLEOTIDE

<400> SEQUENCE: 20
atacagcaaa gatctcggg                                             19

<210> SEQ ID NO: 21
<211> LENGTH: 87
<212> TYPE: DNA
<213> ORGANISM: pUC19FLAD78

<400> SEQUENCE: 21
gaattcggct ttaatacgac tcactatagg atacgatcgg tctgacaatt ggatccgttc  60
```

```
gcgggtcccc tgtacaaagc cgaattc                                          87
```

<210> SEQ ID NO: 22
<211> LENGTH: 64
<212> TYPE: DNA
<213> ORGANISM: pUC18FLBP2

<400> SEQUENCE: 22

```
ttgcatgcct gcaggggggcc cccgcaggcg aagtcgtatc ctatagtgag tcgtattaga    60
attc                                                                  64
```

<210> SEQ ID NO: 23
<211> LENGTH: 3261
<212> TYPE: DNA
<213> ORGANISM: pUC19FLAD78

<400> SEQUENCE: 23

```
ggatacgatc ggtctgaccc cggggagtc acccggggac aggccgtcaa ggccttgttc      60
caggatggga ctcctccttc tacaacgcta tcattgatgg ttagtagaga tcagacaaac    120
gatcgcagcg atgacaaacc tgcaagatca aacccaacag attgttccgt tcatacggag   180
ccttctgatg ccaacaaccg gaccggcgtc cattccggac gacaccctgg agaagcacac   240
tctcaggtca gagacctcga cctacaattt gactgtgggg gacacagggt cagggctaat   300
tgtcttttc cctggattcc ctggctcaat tgtgggtgct cactacacac tgcagggcaa   360
tgggaactac aagttcgatc agatgctcct gactgcccag aacctaccgg ccagttacaa   420
ctactgcagg ctagtgagtc ggagtctcac agtgaggtca agcacacttc ctggtggcgt   480
ttatgcacta acggcacca taaacgccgt gaccttccaa ggaagcctga gtgaactgac   540
agatgttagc tacaatgggt tgatgtctgc aacagccaac atcaacgaca aaattgggaa   600
cgtcctagta ggggaagggg tcaccgtcct cagcttaccc acatcatatg atcttgggta   660
tgtgaggctt ggtgacccca ttcccgcaat agggcttgac ccaaaaatgg tagccacatg   720
tgacagcagt gacaggccca gagtctacac cataactgca gccgatgatt accaattctc   780
atcacagtac caaccaggtg gggtaacaat cacactgttc tcagccaaca ttgatgccat   840
cacaagcctc agcgttgggg gagagctcgt gtttcaaaca agcgtccacg gccttgtact   900
gggcgccacc atctacctca taggctttga tgggacaacg gtaatcacca gggctgtggc   960
cgcaaacaat gggctgacga ccggcaccga caaccttatg ccattcaatc ttgtgattcc  1020
aacaaacgag ataacccagc caatcacatc catcaaactg gagatagtga cctccaaaag  1080
tggtggtcag gcaggggatc agatgtcatg gtcggcaaga gggagcctag cagtgacgat  1140
ccatggtggc aactatccag gggccctccg tcccgtcacg ctagtggcct acgaaagagt  1200
ggcaacagga tccgtcgtta cggtcgctgg ggtgagcaac ttcgagctga tcccaaatcc  1260
tgaactagca aagaacctgg ttacagaata cggccgattt gacccaggag ccatgaacta  1320
cacaaaattg atactgagtg agagggaccg tcttggcatc aagaccgtct ggccaacaag  1380
ggagtacact gactttcgtg aatacttcat ggaggtggcc gacctcaact ctcccctgaa  1440
gattgcagga gcattcggct tcaaagacat aatccgggcc ataaggagga tagctgtgcc  1500
ggtggtctcc acattgttcc cacctgccgc tcccctagcc catgcaattg ggaaggtgt   1560
agactacctg ctgggcgatg aggcacaggc tgcttcagga actgctcgag ccgcgtcagg  1620
aaaagcaaga gctgcctcag gccgcataag gcagctgact ctcgccgccg acaaggggta  1680
```

-continued

```
cgaggtagtc gcgaatctat tccaggtgcc ccagaatccc gtagtcgacg ggattcttgc    1740
ttcacctggg gtactccgcg gtgcacacaa cctcgactgc gtgttaagag agggtgccac    1800
gctattccct gtggttatta cgacagtgga agacgccatg acacccaaag cattgaacag    1860
caaaatgttt gctgtcattg aaggcgtgcg agaagacctc caacctccat ctcaaagagg    1920
atccttcata cgaactctct ctggacacag agtctatgga tatgctccag atggggtact    1980
tccactggag actgggagag actacaccgt tgtcccaata tgatgatgtct gggacgacag    2040 cattatgctg tccaaagatc ccatacctcc tattgtggga aacagtggaa atctagccat    2100
agcttacatg gatgtgtttc gacccaaagt cccaatccat gtggctatga cgggagccct    2160
caatgcttgt ggcgagattg agaaagtaag ctttagaagc accaagctcg ccactgcaca    2220
ccgacttggc cttaggttgg ctggtcccgg agcattcgat gtaaacaccg ggcccaactg    2280
ggcaacgttc atcaaacgtt tccctcacaa tccacgcgac tgggacaggc tcccctacct    2340
caacctacca taccttccac ccaatgcagg acgccagtac caccttgcca tggctgcatc    2400
agagttcaaa gagaccccccg aactcgagag tgccgtcaga gcaatggaag cagcagccaa    2460
cgtggaccca ctattccaat ctgcactcag tgtgttcatg tggctggaag agaatgggat    2520
tgtgactgac atggccaact tcgcactcag cgacccgaac gcccatcgga tgcgaaattt    2580
tcttgcaaac gcaccacaag caggcagcaa gtcgcaaagg gccaagtacg ggacagcagg    2640
ctacggagtg gaggctcggg gccccacacc agaggaagca cagagggaaa aagacacacg    2700
gatctcaaag aagatggaga ccatgggcat ctactttgca acaccagaat gggtagcact    2760
caatgggcac cgagggccaa gccccggcca gctaaagtac tggcagaaca cacgagaaat    2820
accggaccca aacgaggact atctagacta cgtgcatgca gagaagagcc ggttggcatc    2880
agaagaacaa atcctaaggg cagctacgtc gatctacggg gctccaggac aggcagagcc    2940
accccaagct ttcatagacg aagttgccaa agtctatgaa atcaaccatg acgtggccc    3000 aaaccaagaa cagatgaaag atctgctctt gactgcgatg gagatgaagc atcgcaatcc    3060
caggcgggct ctaccaaagc ccaagccaaa acccaatgct ccaacacaga gaccccctgg    3120
tcggctgggc cgctggatca ggaccgtctc tgatgaggac cttgagtgag ctcctggga    3180 gtctcccgac accaccgcg caggtgtgga caccaattcg gccttacaac atcccaaatt    3240
ggatccgttc gcgggtcccc t    3261
```

<210> SEQ ID NO: 24
<211> LENGTH: 2827
<212> TYPE: DNA
<213> ORGANISM: pUCFLBP2

<400> SEQUENCE: 24

```
ggatacgatg ggtctgaccc tctgggagtc acgaattaac gtggctacta ggggcgatac     60
ccgccgctgg ccgccacgtt agtggctcct cttcttgatg attctgccac catgagtgac    120
attttcaaca gtccacaggc gcgaagcacg atctcagcag cgttcggcat aaagcctact    180
gctggacaag acgtggaaga actcttgatc cctaaagttt gggtgccacc tgaggatccg    240
cttgccagcc ctagtcgact ggcaaagttc tcagagaga acggctacaa agttttgcag    300
ccacggtctc tgcccgagaa tgaggagtat gagaccgacc aaatactccc agacttagca    360
tggatgcgac agatagaagg ggctgtttta aaacccactc tatctctccc tattggagat    420
caggagtact tcccaaagta ctacccaaca catcgcccta gcaaggagaa gcccaatgcg    480
tacccgccag acatcgcact actcaagcag atgatttacc tgtttctcca ggttccagag    540
```

-continued

```
gccaacgagg gcctaaagga tgaagtaacc ctcttgaccc aaaacataag ggacaaggcc      600
tatggaagtg ggacctacat gggacaagca aatcgacttg tggccatgaa ggaggtcgcc      660
actggaagaa acccaaacaa ggatcctcta aagcttgggt acactttga gagcatcgcg       720
cagctacttg acatcacact accggtaggc ccacccggtg aggatgacaa gccctgggtg      780
ccactcacaa gagtgccgtc acggatgttg gtgctgacgg gagacgtaga tggcgacttt      840
gaggttgaag attaccttcc caaaatcaac ctcaagtcat caagtggact accatatgta      900
ggtcgcacca aggagagac aattggcgag atgatagcta tctcaaacca gtttctcaga       960
gagctatcaa cactgttgaa gcaaggtgca gggacaaagg ggtcaaacaa gaagaagcta     1020
ctcagcatgt taagtgacta ttggtactta tcatgcgggc ttttgtttcc aaaggctgaa     1080
aggtacgaca aaagtacatg gctcaccaag acccggaaca tatggtcagc tccatcccca     1140
acacacctca tgatctctat gatcacctgg cccgtgatgt ccaacagccc aaataacgtg     1200
ttgaacattg aagggtgtcc atcactctac aaattcaacc cgttcagagg agggttgaac     1260
aggatcgtcg agtggatatt ggccccggaa gaacccaagg ctcttgtata tgcggacaac     1320
atatacattg tccactcaaa cacgtggtac tcaattgacc tagagaaggg tgaggcaaac     1380
tgcactcgcc aacacatgca agccgcaatg tactacatac tcaccagagg gtggtcagac     1440
aacggcgacc caatgttcaa tcaaacatgg gccacctttg ccatgaacat tgcccctgct     1500
ctagtggtgg actcatcgtg cctgataatg aacctgcaaa ttaagaccta tggtcaaggc     1560
agcgggaatg cagccacgtt catcaacaac cacctcttga gcacactagt gcttgaccag     1620
tggaacctga tgagacagcc cagaccagac agcgaggagt tcaaatcaat tgaggacaag     1680
ctaggtatca actttaagat tgagaggtcc attgatgata tcagggggcaa gctgagacag     1740
cttgtcctcc ttgcacaacc agggtacctg agtggggggg ttgaaccaga acaatccagc     1800
ccaactgttg agcttgacct actagggtgg tcagctacat acagcaaaga tctcgggatc     1860
tatgtgccgg tgcttgacaa ggaacgccta ttttgttctg ctgcgtatcc caagggagta     1920
gagaacaaga gtctcaagtc caaagtcggg atcgagcagg catacaaggt agtcaggtat     1980
gaggcgttga ggttggtagg tggttggaac tacccactcc tgaacaaagc ctgcaagaat     2040
aacgcaggcg ccgctcggcg gcatctggag gccaaggggt tcccactcga cgagttccta     2100
gccgagtggt ctgagctgtc agagttcggt gaggccttcg aaggcttcaa tatcaagctg     2160
accgtaacat ctgagagcct agccgaactg aacaagccag tacccccaa gcccccaaat     2220
gtcaacagac cagtcaacac tggggactc aaggcagtca gcaacgccct caagaccggt     2280
cggtacagga acgaagccgg actgagtggt ctcgtccttc tagccacagc aagaagccgt     2340
ctgcaagatg cagttaaggc caaggcagaa gccgagaaac tccacaagtc caagccagac     2400
gaccccgatg cagactggtt cgaaagatca gaaactctgt cagaccttct ggagaaagcc     2460
gacatcgcca gcaaggtcgc ccactcagca ctcgtggaaa caagcgacgc ccttgaagca     2520
gttcagtcga cttccgtgta cacccccaag taccagaaga tcaagaaccc acagaccgcc     2580
tccaaccccg ttgttgggct ccacctgccc gccaagagag ccaccggtgt ccaggccgct     2640
cttctcggag caggaacgag cagaccaatg gggatggagg cccaacacg gtccaagaac      2700
gccgtgaaaa tggccaaacg gcggcaacgc caaaaggaga gccgctaaca gccatgatgg     2760
gaaccactca agaagaggac actaatccca gaccccgtat ccccggcctt cgcctgcggg     2820
ggccccc                                                              2827
```

<210> SEQ ID NO: 25
<211> LENGTH: 2827
<212> TYPE: DNA
<213> ORGANISM: pUBD78B

<400> SEQUENCE: 25

| | | | | | |
|---|---|---|---|---|---|
| ggatacgatg | ggtctgaccc | tctgggagtc | acgaattaac | gtggctacta | ggggcgatac | 60 |
| ccgccgctgg | ctgccacgtt | agtggctcct | cttcttgatg | attctgccac | catgagtgac | 120 |
| attttcaaca | gtccacaggc | gcgaagcacg | atctcagcag | cgttcggcat | aaagcctact | 180 |
| gctggacaag | acgtggaaga | actcttgatc | cctaaagttt | gggtgccacc | tgaggatccg | 240 |
| cttgccagcc | ctagtcgact | ggcaaagttc | tcagagaga | acggctacaa | agttttgcag | 300 |
| ccacggtctc | tgcccgagaa | tgaggagtat | gagaccgacc | aaatactccc | agacttagca | 360 |
| tggatgcgac | agatagaagg | ggctgtttta | aaacccactc | tatctctccc | tattggagat | 420 |
| caggagtact | tcccaaagta | ctacccaaca | catcgcccta | gcaaggagaa | gcccaatgcg | 480 |
| tacccgccag | acatcgcact | actcaagcag | atgatttacc | tgtttctcca | ggttccagag | 540 |
| gccaacgagg | gcctaaagga | tgaagtaacc | ctcttgaccc | aaaacataag | ggacaaggcc | 600 |
| tatggaagtg | ggacctacat | gggacaagca | actcgacttg | tggccatgaa | ggaggtcgcc | 660 |
| actggaagaa | acccaaacaa | ggatcctcta | aagcttgggt | acactttga | gagcatcgcg | 720 |
| cagctacttg | acatcacact | accggtaggc | ccacccggtg | aggatgacaa | gccctgggtg | 780 |
| ccactcacaa | gagtgccgtc | acggatgttg | gtgctgacgg | gagacgtaga | tggcgacttt | 840 |
| gaggttgaag | attaccttcc | caaaatcaac | ctcaagtcat | caagtggact | accatatgta | 900 |
| ggtcgcacca | aggagagac | aattggcgag | atgatagcta | tatcaaacca | gtttctcaga | 960 |
| gagctatcaa | cactgttgaa | gcaaggtgca | gggacaaagg | ggtcaaacaa | gaagaagcta | 1020 |
| ctcagcatgt | taagtgacta | ttggtactta | tcatgcgggc | ttttgtttcc | aaaggctgaa | 1080 |
| aggtacgaca | aaagtacatg | gctcaccaag | acccggaaca | tatggtcagc | tccatcccca | 1140 |
| acacacctca | tgatctccat | gatcacctgg | cccgtgatgt | ccaacagccc | aaataacgtg | 1200 |
| ttgaacattg | aagggtgtcc | atcactctac | aaattcaacc | cgttcagagg | agggttgaac | 1260 |
| aggatcgtcg | agtggatatt | ggccccggaa | gaacccaagg | ctcttgtata | tgcggacaac | 1320 |
| atatacattg | tccactcaaa | cacgtggtac | tcaattgacc | tagagaaggg | tgaggcaaac | 1380 |
| tgcactcgcc | aacacatgca | agccgcaatg | tactacatac | tcaccagagg | gtggtcagac | 1440 |
| aacggcgacc | caatgttcaa | tcaaacatgg | gccacctttg | ccatgaacat | tgcccctgct | 1500 |
| ctagtggtgg | actcatcgtg | cctgataatg | aacctgcaaa | ttaagaccta | tggtcaaggc | 1560 |
| agcgggaatg | cagccacgtt | catcaacaac | cacctcttga | gcacgctagt | gcttgaccag | 1620 |
| tggaacttga | tgagacagcc | cagaccagac | agcgaggagt | tcaaatcaat | tgaggacaag | 1680 |
| ctaggtatca | actttaagat | tgagaggtcc | attgatgata | tcagggcaa | gctgagacag | 1740 |
| cttgtcctcc | ttgcacaacc | agggtacctg | agtgggggg | ttgaaccaga | acaatccagc | 1800 |
| ccaactgttg | agcttgacct | actagggtgg | tcagctacat | acagcaaaga | tctcgggatc | 1860 |
| tatgtgccgg | tgcttgacaa | ggaacgccta | ttttgttctg | ctgcgtatcc | caagggagta | 1920 |
| gagaacaaga | gtctcaagtc | caaagtcggg | atcgagcagg | catacaaggt | agtcaggtat | 1980 |
| gaggcgttga | ggttggtagg | tggttggaac | tacccactcc | tgaacaaagc | ctgcaagaat | 2040 |
| aacgcaggcg | ccgtcggcg | gcatctggag | gccaaggggt | tcccactcga | cgagttccta | 2100 |
| gccgagtggt | ctgagctgtc | agagttcggt | gaggccttcg | aaggcttcaa | tatcaagctg | 2160 |

```
accgtaacat ctgagagcct agccgaactg aacaagccag tacccccaa gcccccaaat    2220 gtcaacagac cagtcaacac tgggggactc aaggcagtca gcaacgccct caagaccggt    2280
cggtacagga acgaagccgg actgagtggt ctcgtccttc tagccacagc aagaagccgt    2340
ctgcaagatg cagttaaggc caaggcagaa gccgagaaac tccacaagtc caagccagac    2400
gaccccgatg cagactggtt cgaaagatca gaaactctgt cagaccttct ggagaaagcc    2460
gacatcgcca gcaaggtcgc ccactcagca ctcgtggaaa caagcgacgc ccttgaagca    2520
gttcagtcga cttccgtgta caccccaag tacccagaag tcaagaaccc acagaccgcc    2580
tccaaccccg ttgttgggct ccacctgccc gccaagagag ccaccggtgt ccaggccgct    2640
cttctcggag caggaacgag cagaccaatg gggatggagg ccccaacacg gtccaagaac    2700
gccgtgaaaa tggccaaacg gcggcaacgc caaaaggaga gccgctaaca gccatgatgg    2760
gaaccactca agaagaggac actaatccca gaccccgtat ccccggcctt cgcctgcggg    2820
ggccccc                                                              2827
```